United States Patent [19]

Ducep et al.

[11] Patent Number: 5,157,116
[45] Date of Patent: Oct. 20, 1992

[54] α-GLUCOSIDASE INHIBITORS

[75] Inventors: Jean-Bernard Ducep, Sundhoffen; Charles Danzin, Strasbourg, both of France

[73] Assignee: Merrell Dow Pharmaceuticals Inc., Cincinnati, Ohio

[21] Appl. No.: 839,014

[22] Filed: Feb. 18, 1992

Related U.S. Application Data

[63] Continuation of Ser. No. 756,945, Sep. 9, 1991, abandoned, which is a continuation-in-part of Ser. No. 353,357, May 17, 1989, abandoned.

[30] Foreign Application Priority Data

Jun. 2, 1988 [EP] European Pat. Off. .......... 88401340

[51] Int. Cl.$^5$ .................. A61K 31/70; A61K 31/715; C07H 19/048; C07H 7/06
[52] U.S. Cl. .................. 536/17.4; 536/18.7; 435/122; 514/24; 514/25; 514/866
[58] Field of Search .......... 514/25, 24, 866; 536/17.4, 17.5; 435/122

[56] References Cited

U.S. PATENT DOCUMENTS

| | | | |
|---|---|---|---|
| 4,182,767 | 1/1980 | Murai et al. | 546/242 |
| 4,220,782 | 9/1980 | Stoltefuss | 546/242 |
| 4,260,622 | 4/1981 | Junge et al. | 544/105 |
| 4,338,433 | 7/1982 | Matsumura et al. | 536/46 |
| 4,405,714 | 9/1983 | Kinast et al. | 435/546 |
| 4,639,436 | 1/1987 | Junge et al. | 514/514 |
| 5,051,407 | 9/1991 | Böshagen et al. | 514/315 |

FOREIGN PATENT DOCUMENTS

| | | |
|---|---|---|
| 0186103 | 7/1986 | European Pat. Off. . |
| 0315017 | 5/1989 | European Pat. Off. . |
| 61-115093 | 6/1986 | Japan . |
| 2181729 | 4/1987 | United Kingdom . |

OTHER PUBLICATIONS

Chemical Abstracts 90:151998n (May 7, 1979, No. 19).
Chemical Abstracts 92:147138j (Apr. 28, 1980, No. 17).
Chemical Abstracts 94:65995p (Mar. 2, 1981, No. 9).
Chemical Abstracts 94:209153n (Jun. 22, 1981, No. 25).
Chemical Abstracts 95:163893u (Nov. 9, 1981, No. 19).
Chemical Abstracts 96:117597y (Apr. 12, 1982, No. 15).
Chemical Abstracts 96:163114m (May 10, 1982, No. 19).
Chemical Abstracts 97:163420d (Nov. 8, 1982, No. 19).
Chemical Abstracts 106:84991s (Mar. 16, 1987, No. 11).
Fleet, George W. J., et al, *FEBS Letters* 237:(12) 128–132 (1988).
Fleet, George W. J., et al, *Tetrahedron* 42(20): 5685–5692 (1986).

*Primary Examiner*—Ronald W. Griffin
*Attorney, Agent, or Firm*—Stephen L. Nesbitt

[57] ABSTRACT

This invention relates to novel N-derivatives of 1-deoxy-nojirimycin, to the processes for their preparation and to their end-use applications, particularly as to their use in the treatment of diabetes.

24 Claims, No Drawings

α-GLUCOSIDASE INHIBITORS

CROSS-REFERENCE TO RELATED APPLICATION

This is a continuation of application Ser. No. 07/756,945, filed Sep. 9, 1991, now abandoned, which is a continuation-in-part of application Ser. No. 07/353,357, filed May 17, 1989, now abandoned.

FIELD OF THE INVENTION

This invention relates to novel N-derivatives of 1-deoxy-nojirimcyin, to the processes for their preparation and to their end-use applications, particularly as to their use in the treatment of diabetes.

More specifically this invention relates to novel N-glycosyl derivatives of 1-deoxy-nojirimycin, to the chemical processes for their preparation, to their α-glucosidase inhibiting properties, and to their end-use application in the treatment of diabetes, obesity and those diseases associated with retroviruses, particularly the HIV virus reported to be the causative of the acquired immune deficiency syndrome (AIDS).

Still more specifically this invention relates, to the novel 1-deoxy nojirimycin derivatives of the formula

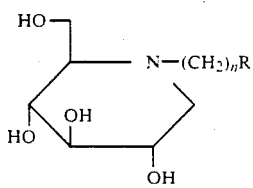

and the pharmaceutically acceptable acid addition salts thereof wherein n is zero, 1 or 2 and R is a glycosyl moiety. The glycosyl moiety represented by "R" in Formula I are radicals which contain from 1 to 3 hexose, pentose or heptose units which optionally bear an ether or an acyl radical at the anomeric carbon atom of the terminal hexose or pentose moiety.

Acid addition salts are those salts forms with such inorganic acids as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, 2-acetoxybenzoic, madelic and like acids; and with organic sulfonic acids such as methane-sulfonic acid and p-toluenesulfonic acid.

In general, the mono-, di- or trisaccharide moiety (i.e., the glycosyl moiety defined by "R") may be attached directly—or thru a $(CH_2)_n$ alkylene bridge—to the nitrogen atom of the 1-deoxynojirimycin moiety thru either an exocyclic or ring carbon atom of the pentose, hexose or heptose unit thereby forming a variety of position isomers for each individual glycosyl moiety. Also, similar or dissimilar pentose, hexose or heptose moieties may be linked to each other thru a glycosidic oxygen bridge wherein the bridging oxygen atom is attached to an exocylic and/or endocyclic carbon atom of the pentose or hexose moiety of which the glycosyl radical is comprised; again the position isomers all being contemplated as being within the scope of this invention.

Exemplary of glycosyl radicals comtemplated by the "R" designation in Formula I are such monosaccharides as 6- or 4-glucosyl, 6- or 4-galactosyl, 4-fucosyl, 1-, 2- or 6-fructosyl, 6- or 4-mannosyl, 4-ribosyl, 4-arabinosyl, 4-xylosyl, 6- or 4-allosyl, 6- or 4-altrosyl, 6- or 4-gulosyl, 6- or 4-idosyl, 6- or 4-talosyl, 4-lyxosyl, and the 6-D- or L-glycero-D-gluco heptosyl, 6-D- or L-glycero-D-manno heptosyl, 6-D- or L-glycero-D-talo heptosyl, 6-D- or L-glycero-D-ido heptosyl, 6-D- or L-glycero-D-allo heptosyl, 6-D- or L-glycero-D-altro heptosyl, 6-D- or L-glycero-D-gulo heptosyl, and 6-deoxy heptoses such as, for example, 6-deoxy-D-manno heptose and 6-deoxy-D-altro heptose, and such disaccharides as 4- or 6-isomaltosyl, 4- or 6-trehalosyl, β 4- or 6-cellobiosyl, maltosyl, and such trisaccharides as maltotriosyl and cellotriosyl. Preferred glycosyl radicals are 6- or 4-glucosyl, 1- or 6-fructosyl, 6- or 4-maltosyl and 6- or 4-isomaltosyl. Ether derivatives are those derivatives wherein the hydroxyl group attached to the anomeric carbon atom is etherified and include the $C_{-8}$ alkyl derivatives, preferably methyl, ethyl, propyl, butyl, pentyl, hexyl, cyclohexyl, cyclohexylmethyl, t-butyl, isobutyl, isopropyl and aromatic derivatives such as phenyl and benzyl and the like. Acyl derivatives, such as those formed at the anomeric carbon atom by reaction of the free hydroxy radical with $C_{1-8}$ alkanoic acids or benzoic acids, are also contemplated even though such acylated moieties may easily be removed from the glycosyl radical. Preferred acyl radicals are those formed with acetic or benzoic acids, although acyl radicals formed from such acids as propionic, n-butyric, isobutyric, n-valeric, hexanoic and phenylacetic acid are contemplated.

The compounds of the present invention are prepared by methods analogously known in the art. It is preferred to condense an appropriately hydroxy protected 1-deoxy-nojirimycin (2) with an appropriately hydroxy protected activated glycosyl moiety, preferably using a triflate or halide, preferably the iodide, but including bromide and chloride and including mesylates or tosylates or other equivalently functioning moieties appreciated by those of ordinary skill in the art. In those instances wherein the 1-deoxy-nojirimycin is coupled with a triflate the reaction is effected by refluxing an admixture of equimolar quantities of the reactants in an alcohol- and water-free solvent, preferably a chlorinated solvent such as chloroform, under an inert atmosphere, preferably under nitrogen or argon, for about 1 to 3 days until the reaction is completed. Following standard procedures for the isolation and purification of the reaction products, the protecting groups are removed to obtain the desired product. Debenzylation is readily effected with standard techniques such as catalytic hydrogenation in an appropriate solvent, e.g. ethanol, using a catalyst such as palladium on carbon, or by transfer hydrogenation using cyclohexene and methanol. In those instances wherein esters were utilized (partially or completely) as the hydroxy protecting groups, it is preferred to first remove the ester group by treatment with an alkali alkoxide, e.g. sodium methoxide, in methanol to hydrolyze the esters and then deprotect the benzyl ethers using the foregoing hydrogenation procedures.

In those instances wherein a glycosyl halide is coupled with the 1-deoxy-nojirimycin the reaction is effected by heating the appropriately hydroxy protected reactants in dry dimethyl formamide (DMF) or other equivalently functioning solvent, at about 60°-90° C. for about 12 to 36 hours, said heating taking place using excess amounts of a weak base ($K_2CO_3$) or a molecular sieve, preferably using excess molar amounts of the halide (up to three times) relative to the amine.

The foregoing reactions are illustrated by the following reaction schemes A, B and C.

Reaction Scheme A

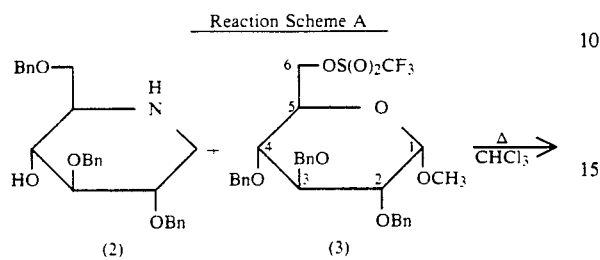

(2)   (3)

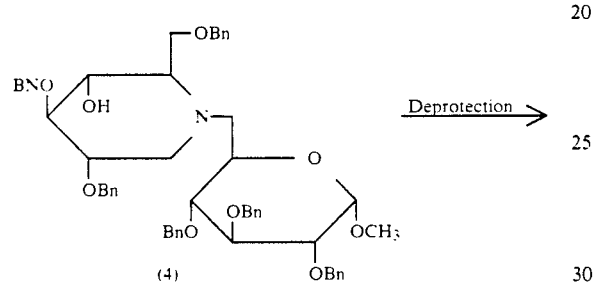

(4)

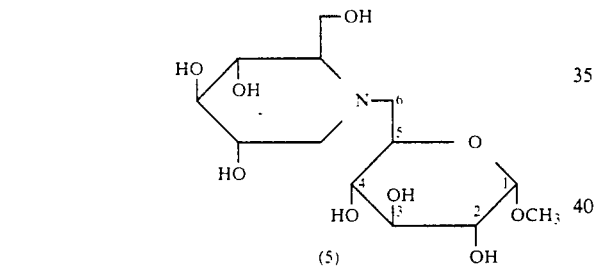

(5)

Reaction Scheme B

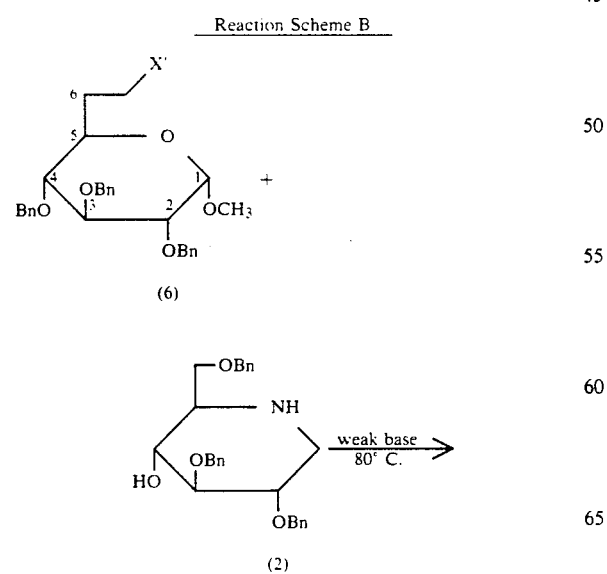

(6)

(2)

-continued

Reaction Scheme B

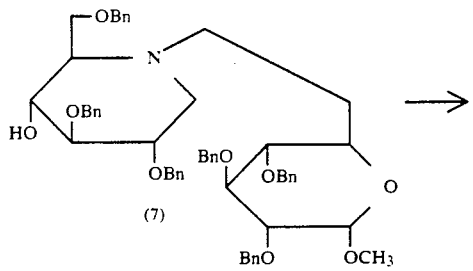

(7)

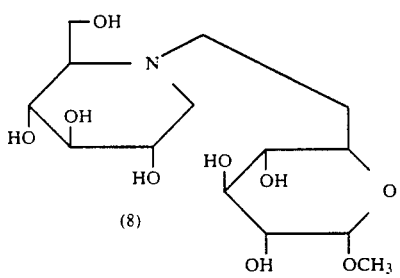

(8)

Illustration of the reaction with a glycosyl moiety containing a heptose unit is depicted in Reaction Scheme C.

Reaction Scheme C

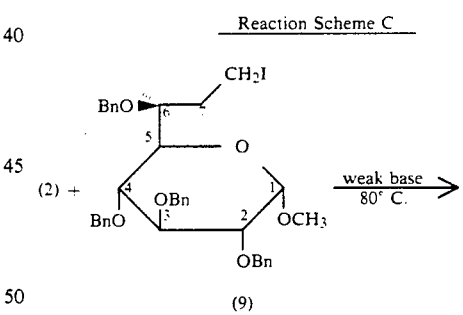

(9)

(10)

-continued
Reaction Scheme C

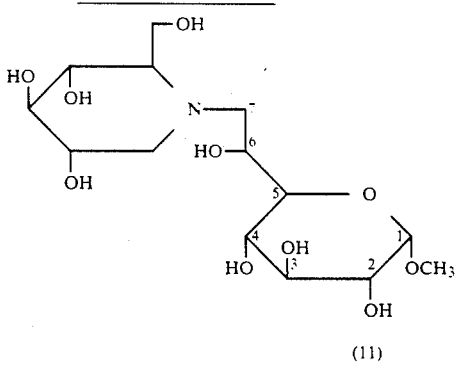

(11)

Otherwise depicted, the reaction scheme may more generally be depicted by the following reaction scheme Reaction Scheme D

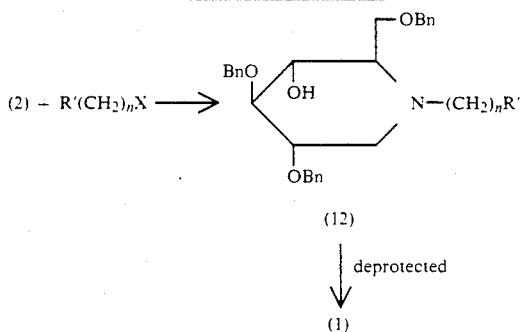

(12)

↓ deprotected (1)

wherein X is a halide (preferably iodide) or a triflate, n is zero, one or two and R' is a hydroxy-protected glycosyl moiety as defined by Formula I, and compound (2) is as depicted in Reaction Schemes A and B.

Appropriately hydroxy protected glycosyl halides (6) and (9), and triflates (3) are those glycosyl radicals (mono-, di- or tri-saccharides of Formula 1) where in the hydroxy groups have been protected with an ester or ether moiety. Preferred esters are the acetate or benzoate esters although other alkanoyl esters, particularly those containing up to six carbon atoms, may be used. The preferred ether is the benzyl ether. Such protected compounds may be prepared by standard procedures very well known and understood in the art.

The glycosyl triflates (of which compound 3 is representative) are prepared by standard procedures such as by reaction of an hydroxy protected glycosyl with trifluoromethylsulfonate anhydride in a chlorinated solvent for about 1-3 hours at about −78° C. to −10° C. (It is to be noted that the anomeric carbon atom which optionally may be etherified or acylated is that carbon atom at the 1-position of the compound of Formula 3, said carbon atom bearing an ether derivative.)

The glycoside halides (of which compounds 6 and 9 is representative) may be prepared by standard techniques starting with an appropriately hydroxy protected glycoside bearing one free hydroxy group. In these instances the alcohol is converted to its aldehyde by a Swern oxidation (treatment with oxalyl chloride in dimethylsulfoxide and triethylamine) followed by an in situ conversion of the aldehyde to an olefin by a Wittig reaction (going through a "ylide" prepared from methyltriphenylphosphonium bromide using one equivalent each of n-butyllithium, potassium t-butoxide and t-butanol in tetrahydrofuran at room temperature for about 4 to 8 hours). The olefin is converted to its corresponding alcohol by hydroboration (treatment with boron dimethylsulfide, under nitrogen, followed by oxidation with hydrogen peroxide and sodium hydroxide). The alcohol is mesylated (treatment with mesyl chloride in $CH_2Cl_2$ in excess $NEt_3$ at −15° C. to 0° C.) and the mesylate converted to its halide (by treatment in ether at 0° C. with magnesium halide), preferably using the iodide.

The 1-deoxy-nojirimycin is prepared by reducing the corresponding δ-lactam of 2,3,6-tribenzyloxy-D-gluconic acid with boron dimethylsulfide followed by treatment with gaseous hydrochloric acid.

The following examples illustrate the processes and techniques suitable for the preparation of the compounds of this invention.

EXAMPLE I

Preparation of 2,3,6-TRI-O-BENZYL-1,5-DIDEOXY-1,5-IMINO-D-GLUCITOL

To a solution of 2,3,6-tri-O-benzyl-5-deoxy-D-gluconic acid δ-lactam (compound described in Examples LXIV to LXIX) (0.75 g, 1.6 mmol) in dry tetrahydrofuran (15 ml) was added a 10 M solution of borane in methyl sulfide (0.58 mL) under nitrogen at 0° C. The mixture was stirred 15 min at 0° C., 30 min at room temperature, then refluxed during 6 h and finally stirred overnight at room temperature. The mixture was cooled to 0° C. and the excess of borane was destroyed with methanol and stirred 1 h at room temperature. The reaction mixture was treated with gazeous hydrochloric acid and refluxed during 1 h. The solvents were evaporated under reduced pressure. The residue was dissolved in ethyl acetate and washed with a saturated aqueous solution of sodium bicarbonate. The organic layer was dried over sodium sulfate, filtered and concentrated under reduced pressure to afford an oil. Flash chromatography on silica gel and elution with ethyl acetate afforded 2,3,6-tri-O-benzyl-1,5-dideoxy-1,5-imino-D-glucitol which crystallized in methanol (0.655 g, 90%); m.p. 73°-74° C.

EXAMPLE II

Preparation of METHYL 2,3,4-TRI-O-BENZYL-6-O-TRIFLUOROMETHYL-SULFONYL-α-D-GLUCOPYRANOSIDE To a solution of dry pyridine (0.46 mL) in methylene chloride (17.5 mL) cooled to −15° C. was added trifluoromethanesulfonic anhydride (0.87 mL). The mixture was stirred during 15 min at −10° C., then methyl 2,3,4-tri-O-benzyl-α-D-glucopyranoside (1.2 g, 2.58 mmol) in methylene chloride (5 mL) was added (P. Kovac, V. Sklenar and C. Glaudemans, Carbohydr. Res. 175, 201 (1988)). The mixture was stirred during 1.5 h at −10° C. The reaction mixture was washed with water. The organic layer was dried over sodium sulfate, filtered and concentrated under reduced pressure to afford an oil. Flash chromatography on silica gel and elution with a 7:3 mixture of hexane and ethyl acetate afforded the expected compound methyl 2,3,4-tri-O-benzyl-6-O-trifluoromethylsulfonyl-α-D-glucopyranoside which was crystallized from hexane (1.43 g, 93%); m.p. 44°-45° C.

EXAMPLE III

Preparation of 2,3,6-TRI-O-BENZYL-1,5-DIDEOXY-1,5-[(2,3,4-TRI-O-BENZYL-6-DEOXY-1-O-METHYL-6-α-D-GLUCOPYRANOSYL)IMINO]-D-GLUCITOL A solution of methyl 2,3,4-tri-O-benzyl-6-O-trifluoromethylsulfonyl-α-D-glucopyranoside (0.7 g, 1.17 mmol) and 2,3,6-tri-O-benzyl-1,5-dideoxy-1,5-imino-D-glucitol (0.509 g, 1.17 mmol) in ethanol-free chloroform (55 mL) was refluxed under nitrogen during 48 h. The mixture was diluted in methylene chloride and washed successively with a saturated aqueous solution of sodium bicarbonate and saturated brine. The organic layer was dried over sodium sulfate, filtered and concentrated under reduced pressure to afford an oil. Flash chromatography on silica gel and elution with a 6:4 mixture of hexane and ethyl acetate afforded the expected compound 2,3,6-tri-O-benzyl-1,5-dideoxy-1,5-[(2,3,4-tri-O-benzyl-6-deoxy-1-O-methyl-6-α-D-glucopyranosyl)imino]-D-glucitol which was crystallized from methanol (0.772 g, 75%); m.p. 102°-103° C.

EXAMPLE IV

Preparation of 1,5-DIDEOXY-1,5-[(6-DEOXY-1-O-METHYL-6-α-D-GLUCOPYRANOSYL)IMINO]-D-GLUCITOL 2,3,6-tri-O-benzyl-1,5-dideoxy-1,5-[(2,3,4-tri-O-benzyl-6-deoxy-1-O-methyl-6-α-D-glucopyranosyl)imino]-D-glucitol (0.646 g, 0.73 mmol) was dissolved in methanol (20 mL), cyclohexene (10 mL) and Palladium hydroxyde 20% on charcoal (1.2 g) were added. The mixture was degazed and refluxed 24 h under argon atmosphere. The catalysor was filtered and washed twice with methanol. The solvents were evaporated under reduced pressure. The residue was dissolved in water, the aqueous phase was extracted twice with ethyl acetate. The aqueous layer was put to dryness under reduced pressure to afford a foam. Flash chromatography on silica gel and elution with a 50:50:4 mixture of methanol, chloroform and water afforded the expected compound 1,5-dideoxy-1,5-[(6-deoxy-1-O-methyl-6-α-D-glucopyranosyl)imino]-D-glucitol as a foam (0.13 g, 52%).

EXAMPLE V

Preparation of METHYL 2,3,4-TRI-O-BENZYL-6,7-DIDEOXY-α-D-GLUCOHEPT-6-ENOPYRANOSIDE To a solution of oxalyl chloride (1.05 mL, 17.22 mmol) in dry tetrahydrofuran (40 mL) cooled to −78° C., dry dimethyl sulfoxyde (1.3 mL, 18.04 mmol) was added dropwise and then stirred during 35 min at −35° C. The reaction mixture was cooled again to −78° C. and methyl 2,3,4-tri-O-benzyl-α-D-glucopyranoside (6 g, 16.4 mmol) dissolved in tetrahydrofuran (20 mL) was added and the mixture was stirred during 15 min at −35° C., then triethylamine (11.5 mL, 82.65 mmol) was added and the mixture was stirred during 1 h at −35° C. This aldehyde was used without purification and isolation in a Wittig reaction described as follows. To dried triphenylmethylphosphonium bromide (11.7 g, 32.8 mmol) suspended in tetrahydrofuran (700 mL) was added dropwise at −78° C. a 1.42 M solution of n-butyl-lithium in hexane (23 mL, 32.66 mmol). The reaction mixture was warmed to room temperature and stirred during 1.5 h. Then the mixture was cooled to 0° C. and potassium tertio-butylate (3.68 g, 32.8 mmol) and dry tertio-butyl alcohol (3mL, 31.8 mmol) were added. The mixture was stirred again at room temperature during 30 min. The reaction mixture was cooled to −78° C. and the tetrahydrofuran solution of the aldehyde prepared above was added dropwise. The reaction mixture was warmed to room temperature and stirred during 2 h. A saturated aqueous solution of ammonium chloride and the solvents were evaporated under reduced pressure. The residue was dissolved in ether and washed with water. The organic layer was dried over sodium sulfate, filtered and concentrated under reduced pressure to afford a brown oil. Flash chromatography on silica gel and elution with a 4:96 mixture of ethyl acetate and toluene afforded the expected olefine methyl 2,3,4-tri-O-benzyl-6,7-dideoxy-α-D-glucohept-6-enopyranoside (3.26 g, 55%) which crystallized from hexane; m.p. 46°-47° C.

EXAMPLE VI

Preparation of METHYL 2,3,4-TRI-O-BENZYL-6-DEOXY-α-D-GLUCOHEPTOPYRANOSIDE

To a solution of methyl 2,3,4-tri-O-benzyl-6,7 dideoxy-α-D-glucohept-6-enopyranoside (0.878 g, 2.43 mmol) in dry tetrahydrofuran (5 mL) was added a 10 M solution of borane in methyl sulfide (0.24 mL, 2.4 mmol) at 0° C. under nitrogen. The mixture was stirred during 3 h at room temperature. The excess of borane was destroyed with ethanol (1 mL). The mixture was cooled at 0° C. 30% hydrogen peroxyde (0.3 mL) were added. The mixture was refluxed during 2 h. The reaction mixture was diluted with water and extracted three times with ether. The organic layer was dried over sodium sulfate, filtered and concentrated under reduced pressure to afford an oil. Flash chromatography on silica gel and elution with a 1:1 mixture of ethyl acetate and hexane afforded the expected alcohol methyl 2,3,4-tri-O-benzyl-6-deoxy-α-D-glucoheptopranoside (0.414 g, 45%) which crystallized from hexane; m.p. 50°-53° C.

EXAMPLE VII

Preparation of METHYL 2,3,4-TRI-O-BENZYL-6-DEOXY-7-O-METHYLSULFONYL-α-D-GLUCOHEPTOPYRANOSIDE To a solution of methyl 2,3,4-tri-O-benzyl-6-deoxy-7-O-methylsulfonyl-α-D-glucoheptopyranoside (0.38 g, 0.83 mmol) in dry methylene chloride (10 mL) was added triethylamine (0.2 mL, 1.43 mmol). Then the solution was cooled to −10° C. and mesylchloride (0.08 mL), 1 mmol) was added. The mixture was stirred an additional 15 min at −10° C., then the reaction was allowed to warm up to room temperature. The mixture was washed three times with water. The organic phase was dried over sodium sulfate, filtered and concentrated under reduced pressure to afford a yellow oil. Flash chromatography on silica gel and elution with a 40:60 mixture of ethyl acetate and hexane afforded the expected mesylate methyl 2,3,4-tri-O-benzyl-6-deoxy-7-O-methylsulfonyl-α-D-glucoheptopyranoside as an oil (0.38 g, 91%).

EXAMPLE VIII

Preparation of METHYL 2,3,4-TRI-O-BENZYL-6,7-DIDEOXY-7-IODO-α-D-GLUCOHEPTOPYRANOSIDE To a solution of methyl 2,3,4-tri-O-benzyl-6-deoxy-7-O-methylsulfonyl-D-glucoheptopyranoside (0.38 g, 0.83 mmol) in ether (5 mL) was added at 0° C. a 0.375 M solution of magnesium iodide (6.7 mL). The mixture was stirred 15 min at 0° C. The excess of magnesium iodide was hydrolyzed with water. The reaction mixture was washed with sodium thiosulfate and water. The organic layer was dried over sodium sulfate, filtered and concentrated under reduced pressure to afford an oil. Flash chromatography on silica gel and elution with a 2:8 mixture of ethyl acetate and hexane afforded the expected iodide methyl 2,3,4-tri-O-benzyl-6,7-dideoxy-7-iodo-α-D-glucoheptopyranoside which was crystallized from hexane (0.368 g, 91%); m.p. 66°–68° C.

EXAMPLE IX

Preparation of 2,3,6-TRI-O-BENZYL-1,5-DIDEOXY-1,5-[(2,3,4-TRI-O-BENZYL-6,7-DIDEOXY-1-O-METHYL-7-α-D-GLUCOHEPTOPYRANOSYL)IMINO]-D-GLUCITOL A solution of methyl 2,3,4-tri-O-benzyl-6,7-dideoxy-7-iodo-α-D-glucoheptopyranoside (0.338 g, 0.69 mmol) and 2,3,6-tri-O-benzyl-1,5-dideoxy-1,5-imino-D-glucitol (0.1 g, 0.23 mmol) in dry dimethylformamide (3 mL) was heated at 80° C. overnight along with dry potassium carbonate (0.127 g, 0.92 mmol). The dimethylformamide was evaporated under reduced pressure. The residue was taken with ethyl acetate and washed twice with water. The organic layer was dried over sodium sulfate, filtered and concentrated under reduced pressure to afford an oil. Chromatography on neutral alumine activity III and elution with a 8:2 mixture of hexane and ethyl acetate afforded the expected amine 2,3,6-tri-O-benzyl-1,5-dideoxy-1,5-[(2,3,4-tri-O-benzyl-6,7-dideoxy-1-O-methyl-7-α-D-glucoheptopyranosyl)imino]-D-glucitol which was crystallized in methanol (0.125 g, 60%); m.p. 42°–43° C.

EXAMPLE X

Preparation of 1,5-DIDEOXY-1,5-[(6,7-DIDEOXY-1-O-METHYL-7-α-D-GLUCOHEPTOPYRANOSYL)IMINO]-D-GLUCITOL 2,3,6-tri-O-benzyl-1,5-dideoxy-1,5-[(2,3,4-tri-O-benzyl-6,7-dideoxy-1-O-methyl-7-α-D-glucoheptopyranosyl)imino]-D-glucitol (0.1 g, 0.11 mmol) was dissolved in methanol (10 mL) containing ethyl acetate (0.1 mL) and water (1 mL). Palladium hydroxyde 20% on charcoal (0.05 g) was added. The mixture was hydrogenated at 1 atmosphere during two weeks. The catalysor was removed filtration and the solvents were evaporated under reduced pressure. Crystallization of the residue from isopropanol afforded the expected amine 1,5-dideoxy-1,5-[(6,7-dideoxy-1-O-methyl-7-α-D-glucoheptopyranosyl)imino]-D-glucitol (0.023 g, 58%).

EXAMPLE IX

Preparation of 2,3,6-TRI-O-BENZYL-1,5-DIDEOXY-1,5-[(1-DEOXY-2,3:4,5-DI-O-ISOPROPYLIDENE-β-D-FRUCTOPYRANOSYL)IMINO]-D-GLUCITOL A solution of 2,3:4,5-di-O-isopropylidene-1-O-trifluoromethylsulfonyl-β-D-fructopyranose (1.20 g, 3.06 mmol) (P. J. Card and W. D. Hitz, J. Amer. Chem. Soc., 106, 5348 (1984)) and 1,5-dideoxy-2,3,6,-tri-O-benzyl-1,5-imino-D-glucitol (1.331 g, 3.06 mmol) in ethanol-free chlororform (70 ml) is refluxed under nitrogen during 60 h. The mixture is diluted with methylene chloride and washed successively with a saturated aqueous solution bicarbonate and saturated brine. The organic layer is dried over sodium sulfate, filtered and concentrated under reduced pressure to afford an oil. Flash chromatography on silica gel and elution with graded mixture of hexane and ethyl acetate will afford the expected amine 2,3,6-tri-O-benzyl-1,5-[(1-deoxy-2,3:4,5-di-O-isopropylidene-β-D-fructopyranosyl)imino]-D-glucitol as an oil.

EXAMPLE XII

Preparation of 2,3,6-TRI-O-BENZYL-1,5-DIDEOXY-1,5-[(1-DEOXY-2-O-METHYL-α-D-FRUCTOFURANOSYL)IMINO]-D-GLUCITOL 2,3,6-tri-O-benzyl-1,5-dideoxy-1,5-[(1-deoxy-2,3:4,5-di-O-isopropylidene-β-D-fructopyranosyl)imino]-D-glucitol (1.4 g, 2.074 mmol) is dissolved in methanol (100 mL) containing 2% of dry hydrochloric acid. The mixture is refluxed during 48 h. The mixture is neutralized with Amberlyst A 26 OH⁻ form and filtered. The solvents are evaporated under reduced pressure. Flash chromatography on silica gel and elution with graded mixture of ethyl acetate and methanol will afford the expected amine 2,3,6-tri-O-benzyl- 1,5-dideoxy-1,5-[(1-dexoy-2-Omethyl-α-D-fructofuranosyl)-imino]-D-glucitol.

EXAMPLE XIII

Preparation of 1,5-DIDEOXY-1,5-[(1-DEOXY-2-O-METHYL-α-D-FRUCTOFURANOSYL)IMINO]-D-GLUCITOL The amine 2,3,6-tri-O-benzyl-1,5-dideoxy-1,5-[(1-deoxy-2-O-methyl-α-D-fructofuranosyl)imino]-D-glucitol (0.617 g, 1.014 mmol) is dissolved in methanol (25 mL) containing water (2.5 mL), palladium hydroxide 20% on charcoal (0.3 g) is added. The mixture is hydrogenated during 4 days at atmospheric pressure. The catalyst is removed by filtration and the solvents are evaporated under reduced pressure. Flash chromatography on silica gel and elution with graded mixture of chloroform, methanol and water will afford the expected amine 1,5-dideoxy-1,5-[(deoxy-2-O-methyl-α-D-fructofuranosyl)imino]-D-glucitol as an amorphous solid.

EXAMPLE XIV

Preparation of METHYL 2,3,6-TRI-O-BENZYL-4-O-TRIFLUOROMETHYLSULFONYL-α-D-GALACTOPYRANOSIDE To a solution of dry pyridine (0.46 mL) in methylene chloride (17.5 mL) cooled to −15° C. is added trifluoromethane sulfonic anhydride (0.87 mL). The mixture is stirred during 15 min at −10° C., then methyl 2,3,6-tri-O-benzyl-α-D-galactopyranoside (1.2 g, 2.58 mmol) in methylene chloride (5 mL) is added (N. Morishima, S. Koto, M. Oshima, A. Sugimoto and S. Zen, Bull. Chem. Soc. Jpn, 56, 2849 (1983)). The mixture is washed with water. The organic layer is dried over sodium sulfate, filtered and concentrated under reduced pressure so as to afford an oil which is the expected triflate methyl 2,3,6-tri-O-benzyl-4-O-trifluoromethylsulfonyl-α-D-galactopyranoside.

EXAMPLE XV

Preparation of
2,3,6-TRI-O-BENZYL-1,5-DIDEOXY-1,5-[(2,3,6-TRI-O-BENZYL-4-DEOXY-1-O-METHYL-4-α-D-GLUCOPYRANOSYL)IMINO]-D-GLUCITOL A solution of methyl 2,3,6-tri-O-benzyl-4-O-trifluoromethyfulfonyl-α-D-galactopyranoside (1.25 g, 2.53 mmol) and 2,3,6-tri-O-benzyl-1,5-dideoxy-1,5-imino-D-glucitol (1.098 g, 2.53 mmol) in ethanol-free chloroform (70 mL) is refluxed under nitrogen during 3 days. The mixture is diluted with methylene chloride and washed successively with a saturated aqueous solution of sodium bicarbonate and saturated brine. The organic layer is dried over sodium sulfate, filtered and concentrated under reduced pressure so as to afford an oil. Flash chromatography on silica gel and elution with graded mixture of hexane and ethyl acetate will afford the expected amine 0,3,6-tri-O-benzyl-1,5-dideoxy-1,5-[(2,3,6-tri-O-benzyl-4-deoxy-1-O-methyl-4-α-D-glucopyranosyl)imino]-D-glucitol as an oil.

EXAMPLE XVI

Preparation of
1,5-DIDEOXY-1,5-[(4-DEOXY-1-O-METHYL-4-α-D-GLUCOPYRANOSYL)IMINO]-D-GLUCITOL The amine 2,3,6-tri-O-benzyl-1,5-dideoxy-1,5-[(2,3,6-tri-O-benzyl-4-deoxy-1-O-methyl-α-D-glucopyranosyl)imino]-D-glucitol (0.911 g, 1.03 mmol) is dissolved in methanol (20 mL). Cyclohexene (10 mL) and Palladium hydroxyde 20% on charcoal are added. The mixture is degazed and refluxed 16 h under argon atmosphere. The catalysor is filtered and washed twice with methanol. The solvents are evaporated under reduced pressure. The residue is dissolved in water. The aqueous phase is extracted twice with ethyl acetate. The aqueous layer is put to dryness under reduced pressure so as to afford a foam. Flash chromatography on silica gel and elution with a 50:50:4 mixture of methanol, chloroform and water will afford the expected amine 1,5-dideoxy-1,5-[(4-deoxy-1-O-methyl-4-α-D-glucopyranosyl)imino]-D-glucitol as a foam.

EXAMPLE XVII

Preparation of METHYL
2,3,4-TRI-O-BENZYL-6-O-(2,3,4-TRI-O-BENZYL-6-O-TRIFLUOROMETHYLSULFONYL-α-D-GLUCOPYRANOSYL-α-D-GLUCOPYRANOSIDE To a solution of dry pyridine (0.24 mL) in methylene chloride (25 mL) cooled to −15° C. is added trifluoromethane sulfonic anhydride (0.45 mL). The mixture is stirred during 15 min at −10° C., then methyl 6-O-(2,3,4-tri-O-benzyl-α-D-glucopyranosyl)-2,3,4-O-benzyl-α-D-glucopyranoside 91.2 g, 1.34 mmol) in methylene chloride (5 mL) is added (R. Eby and C. Schuerch, Carbohydr. Res., 50, 203 (1976)). The mixture is stirred during 1.5 h at −10° C. The reaction mixture is washed with water. The organic layer is dried over sodium sulfate, filtered and concentrated under reduced pressure so as to afford an oil (1.35 g, 98%) which will be the expected triflate methyl2,3,4-tri-O-benzyl-6-O-(2,3,4-tri-O-benzyl-6-O-trifluoromethylsulfonyl-α-D-glucopyranosyl)-α-D-glucopyranoside.

EXAMPLE XVIII

Preparation of
2,3,6-TRI-O-BENZYL-1,5-DIDEOXY-N-[2,3,4-TRI-O-BENZYL-6-DEOXY-1-(2,3,4-TRI-O-BENZYL-1-O-METHYL-6-O-α-D-GLUCOPYRANOSYL)-α-D-GLUCOPYRANOSYL]-1,5-IMINO-D-GLUCITOL A solution of methyl 2,3,4-tri-O-benzyl-6-O-(2,3,4-tri-O-benzyl-6-O-trifluoromethysulfonyl-α-D-glucopyranosyl)-α-D-glucopyranoside (1.35 g, 1.31 mmol) and 2,3,6-tri-O-benzyl-1,5-dideoxy-1,5-imino-D-glucitol (0.567 g, 1.31 mmol) in ethanol-free chloroform (50 mL) is refluxed under nitrogen during 48 h. The mixture is diluted with methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with graded mixture of hexane and ethyl acetate will afford the expected amine 2,3,6-tri-O-benzyl-1,5-dideoxy-N-[2,3,4-tri-O-benzyl-6-deoxy-1-(2,3,4-tri-O-benzyl-1-O-benzyl-1-O-methyl-6-O-α-D-glucopyranosyl)-α-D-glucopyranosyl]-1,5-imino-D-glucitol as a foam.

EXAMPLE XIX

Preparation of
1,5-DIDEOXY-N-[6-DEOXY-1-(1-O-METHYL-6-O-α-D-GLUCOPYRANOSYL)-α-D-GLUCOPYRANOSYL]-1,5-IMINO-D-GLUCITOL The amine 2,3,6-tri-O-benzyl-1,5-dideoxy-N-[2,3,4-tri-O-benzyl-6-deoxy-1-(2,3,4-tri-O-benzyl-1-O-methyl-6-O-α-D-glucopyranosyl)-α-D-glucopyranosyl]-1,5-imino-D-glucitol (1.2 g, 0.915 mmol) is dissolved in methanol (30 mL). Palladium hydroxyde 20% on charcoal (0.5 g) is added. The mixture is hydrogenated during 4 days at 3 atmosphere. The catalyst is removed by filtration and the solvents are evaporated under reduced pressure. Flash chromatography on 11 TM silica gel and elution with graded mixture of chloroform, methanol and water will afford the expected amine 1,5-dideoxy-N-[6-deoxy-1-(1-O-methyl-6-O-α-D-glucopyranosyl)-α-D-glucopyranosyl]-1,5-imino-D-glucitol as a foam.

EXAMPLE XX

Preparation of METHYL
6-O-(2,3,4-TRI-O-BENZYL-6,7-DIDEOXY-α-D-GLUCOHEPT-6-ENOPYRANOSYL)-2,3,4-TRI-O-BENZYL-α-D-GLUCOPYRANOSIDE To a solution of oxalyl chloride (0.37 mL, 5.97 mmol) in dry tetrahydrofuran (40 mL) cooled to −78° C., dry dimethyl sulfoxyde (0.45 mL, 6.26 mmol) is added dropwise and then stirred during 35 min at −35° C. The reaction mixture is cooled again to −78° C. and methyl 6-O-(2,3,4-tri-O-benzyl-α-D-glucopyranosyl)-2,3,4-tri-O-benzyl-α-D-glucopyranoside (5.1 g, 5.69 mmol) dissolved in tetrahydrofuran (20 mL) is added and the mixture is stirred during 15 min at −35° C., then triethylamine (3.96 mL, 28.45 mmol) is added and the mixture is stirred during 1 h at -35° C. This aldehyde is to be used without purification and isolation in a Wittig reaction described as follows. To dried triphenylmethylphosphonium bromide (4.059 g, 11.38 mmol) suspended in tetrahydrofuran (100 mL) is added dropwise at −78° C. a 1.55 M solution of n-butyllithium in hexane (7.34 mL, 11.38 mmol). The reaction mixture is warmed to room temperature and stirred during 1.5 h. Then the mixture is cooled to 0° C. and potassium tertio-butylate (1.275 g, 11.38 mmol) and dry tertio-butyl alcohol (1.04 mL, 11.38 mmol) are added. The mixture is stirred again at room temperature during 30 min. The reaction mixture is cooled to −78° C. and the tetrahydrofuran solution of the aldehyde prepared above is added dropwise. The reaction mixture is warmed to room temperature and stirred during 2 h. A saturated aqueous solution of ammonium chloride and the solvents are evaporated under reduced pressure. The residue is dissolved in ethyl acetate and washed with water. The organic layer is dried over sodium sulfate, filtered and concentrated under reduced pressure so as to afford a brown oil. Flash chromatography on silica gel and elution with a graded mixture of carbon tetrachloride and ethyl acetate will afford the expected olefine methyl 6-O-(2,3,4-tri-O-benzyl-6,7-dideoxy-α-D-glucohept-6-enopyranosyl)-2,3,4-tri-O-benzyl-α-D-glucopyranoside as an amorphous solid.

EXAMPLE XXI

Preparation of METHYL 6-O-(2,3,4-TRI-O-BENZYL-6-DEOXY-α-D-GLUCOHEPTOPYRANOSYL)-2,3,4-TRI-O-BENZYL-α-D-GLUCOPYRANOSIDE To a solution of methyl 6-O-(2,3,4-tri-O-benzyl-6,7-di-deoxy-α-D-glucohept-6-enopyranosyl)-2,3,4-tri-O-benzyl-α-D-glucopyranoside (2.54 g, 2.85 mmol) in dry tetrahydrofuran (10 mL) is added a 10 M solution of borane in methyl sulfide (0.28 mL, 2.8 mmol) at 0° C. under nitrogen. The mixture is stirred during 3 h at room temperature. Then the mixture is cooled to 0° C. The excess of borane is destroyed with ethanol (1 mL). The mixture is cooled at 0° C. 30% hydrogen peroxyde (0.3 mL) and 3 N aqueous solution of sodium hydroxyde (0.3 mL) are to be added. The mixture is refluxed during 2 h. The reaction mixture is diluted with water and extracted three times with ethyl acetate. The organic layer is dried over sodium sulfate, filtered and concentrated under reduced pressure so as to afford a foam. Flash chromatography on silica gel and elution with a graded mixture of carbon tetrachloride and ethyl acetate will afford the expected alcohol methyl 6-O-(2,3,4-tri-O-benzyl-6-deoxy-α-D-glucoheptopyranosyl)-2,3,4-tri-O-benzyl-α-D-glucopyranoside as a foam.

EXAMPLE XXII

Preparation of METHYL 6-O-(2,3,4-TRI-O-BENZYL-6,7-DIDEOXY-7-IODO-α-D-GLUCOHEPTOPYRANOSYL)-2,3,4-TRI-O-BENZYL-α-D-GLUCOPYRANOSIDE To a solution of methyl 6-O-(2,3,4-tri-O-benzyl-6-deoxy-α-D-glucoheptopyranosyl)-2,3,4-tri-O-benzyl-α-D-glucopyranoside (1.245 g, 1.37 mmol) in dry methylene chloride (15 mL) is added triethylamine (0.29 mL, 2.05 mmol). Then the solution is cooled to −10° C., and mesylchloride (0.11 mL, 1.42 mmol) is added dropwise. The mixture is stirred an additional 15 min at −10° C., then the reaction mixture is washed three times with water. The organic layer is dried over sodium sulfate, filtered and concentrated under reduced pressure so as to afford a foam which is to be used without further purification. The crude methyl 6-O-(2,3,4-tri-O-benzyl-6-deoxy-7-O-methylsulfonyl-α-D-glucoheptopyranosyl)-2,3,4-tri-O-benzyl-α-D-glucopyranoside is dissolved in ether (20 mL). To this mixture a 0.35 M solution of magnesium iodide in ether (17.5 mL) is added dropwise at 0° C. The excess of magnesium iodide is hydrolyzed with water. The reaction mixture is washed with sodium thiosulfate and water. The organic layer is dried over sodium sulfate, filtered and concentrated under reduced pressure to afford a foam. Flash chromatography on silica gel and elution with a graded mixture of carbon tetrachloride and ethyl acetate will afford the expected iodide methyl 6-O-(2,3,4-tri-O-benzyl-6,7-dideoxy-7-iodo-α-D-glucoheptopyranosyl)-2,3,4-tri-O-benzyl-α-D-glucopyranoside as a foam.

EXAMPLE XXIII

Preparation of 2,3,6-TRI-O-BENZYL-1,5-DIDEOXY-N-[2,3,4-TRI-O-BENZYL-6,7-DIDEOXY-1-(2,3,4-TRI-O-BENZYL-1-O-METHYL-6-O-α-D-GLUCOPYRANOSYL)-7-α-D-GLUCOHEPTOPYRANOSYL]-1,5-IMINO-D-GLUCITOL A solution of the iodide methyl 6-O-(2,3,4-tri-O-benzyl-6,7-dideoxy-7-iodo-α-D-glucoheptopyranosyl)-2,3,4-tri-O-benzyl-α-D-glucopyranoside (1.145 g, 1.122 mmol) and the amine 2,3,6-tri-O-benzyl-1,5-dideoxy-1,5-imino-D-glucitol (0.162 g, 0.374 mmol) in dry dimethylformamide (4mL) is heated at 80° C. overnight along with dry potassium carbonate (0.206 g, 1.49 mmol). The dimethylformamide is evaporated under reduced pressure. The residue is taken with ethyl acetate and washed twice with water. The organic layer is dried over sodium sulfate, filtered and concentrated under reduced pressure so as to afford a foam. Chromatography on neutral aluminum oxide activity III and elution with a graded mixture of carbon tetrachloride and ethyl acetate will afford the expected amine 2,3,6-tri-O-benzyl-1,5-dideoxy-N-[2,3,4-tri-O-benzyl-6,7-dideoxy-1-(2,3,4-tri-O-benzyl-1-O-methyl-6-O-α-D-glucopyranosyl)-7-α-D-glucoheptopyranosyl]-1,5-imino-D-glucitol as a foam.

EXAMPLE XXIV

Preparation of 1,5-DIDEOXY-N-[6,7-DIDEOXY-1-(1-O-METHYL-6-O-α-D-GLUCOPYRANOSYL)-7-α-D-GLUCOHEPTOPYRANOSYL]-1,5-IMINO-D-GLUCITOL The amine 2,3,6-tri-O-benzyl-1,5-dideoxy-N-[2,3,4-tri-O-benzyl-6,7-dideoxy-1-(2,3,4-tri-O-benzyl-1-O-methyl-6-O-α-D-glucopyranosyl)-α-D-glucoheptopyranosyl]-1,5-imino-D-glucitol (0.337 g, 0.254 mmol) is dissolved in methanol (30 mL). Palladium hydroxyde 20% on charcoal (0.4 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-[6,7-dideoxy-1-(1-O-methyl-6-O-α-D-glucopyranosyl)-7-α-D-glucoheptopyranosyl]-1,5-imino-D-glucitol as an amorphous solid.

EXAMPLE XXV

Preparation of METHYL 2,3,6-TRI-O-BENZYL-4-CYANO-4-DEOXY-α-D-GLUCOPYRANOSIDE

A solution of methyl 2,3,6-tri-O-benzyl-4-O-trifluoromethylsulfonyl-α-D-galactopyranoside (3 g, 6.07 mmol) and tetra-n-butyl ammonium cyanide (6.51 g, 24.28 mmol) in ethanol-free chloroform (60 mL) is refluxed under nitrogen during 24 h. The reaction mixture is diluted with methylene chloride, washed twice with water. The organic layer is dried over sodium sulfate, filtered and concentrated under reduced pressure so as to afford an oil. Flash chromatography on silica gel and elution with a graded mixture of hexane and ethyl acetate will afford the expected nitrile methyl 2,3,6-tri-O-benzyl-4-cyano-4-deoxy-α-D-glucopyranoside as an oil.

EXAMPLE XXVI

Preparation of METHYL 2,3,6-TRI-O-BENZYL-4-DEOXY-4-FORMYL-α-D-GLYCOPYRANOSIDE

To a solution of methyl 2,3,6-tri-O-benzyl-4-cyano-4-deoxy-α-D-glucopyranoside (1.75 g, 3.7 mmol) in dry tetrahydrofuran (10 mL) is added dropwise at −78° C. a 1.2 M solution of diisobutyl aluminum hydride in n-hexane (3.1 mL). The mixture is stirred under argon at −78° C. during 3 h. Methanol (2 mL) is added and the mixture is warmed to 0° C. Then the solvents are evaporated under reduced pressure. Ether (50 mL) and 0.1 N aqueous hydrochloric acid (40 mL) are added, the mixture is stirred at 0° C. during 1 h. Then after decantation the organic layer is dried over sodium sulfate, filtered and concentrated under reduced pressure so as to afford the expected aldehyde methyl 2,3,6-tri-O-benzyl-4-deoxy-4-formyl-α-D-glucopyranoside as an oil which is used without purification.

EXAMPLE XXVII

Preparation of METHYL 2,3,6-TRI-O-BENZYL-4-DEOXY-4-HYDROXYMETHYL-α-D-GLUCOPYRANOSIDE The aldehyde methyl 2,3,6-tri-O-benzyl-4-deoxy-4-formyl-α-D-glucopyranoside (1.7 g, 3.57 mmol) is dissolved in ethanol (15 mL). The mixture is cooled to 0° C. and solid sodium borohydride (0.068 g, 1.8 mmol) is added portionwise. The mixture is stirred 1 h at 0° C. Then acetic acid (0.4 mL) is added and the solvents are evaporated under reduced pressure. The residue is taken upwith ethyl acetate and washed with saturated aqueous sodium bicarbonate and saturated brine. The organic layer is dried over sodium sulfate, filtered and concentrated under reduced pressure so as to afford an oil. Flash chromatography over silica gel and elution with a graded mixture of hexane and ethyl acetate will afford the expected alcohol methyl 2,3,6-tri-O-benzyl-4-deoxy-4-hydroxy-methyl-α-D-glucopyranoside as an oil.

EXAMPLE XXVIII

Preparation of METHYL 2,3,6-TRI-O-BENZYL-4-DEOXY-4-TRIFLUOROMETHYLSULFONYLOXYMETHYL-α-D-GLUCOPYRANOSIDE To a solution of dry pyridine (0.45 mL) in methylene chloride (30 mL) cooled to −15° C. is added trifluoromethanesulfonic anhydride (0.84 mL). The mixture is stirred during 15 min at −10° C., then methyl 2,3,6-tri-O-benzyl-4-deoxy-4-hydroxymethyl-α-D-glucopyranoside (1.19 g, 2.49 mmol) in methylene chloride (5 mL) is added. The mixture is stirred during 1.5 h at −10° C. The reaction mixture is washed with water. The organic layer is dried over sodium sulfate, filtered and concentrated under reduced pressure so as to afford an oil which is the expected triflate methyl 2,3,6-tri-O-benzyl-4-deoxy-4-trifluoromethylsulfonyloxymethyl-α-D-glucopyranoside.

EXAMPLE XXIX

Preparation of 2,3,6-TRI-O-BENZYL-1,5-DIDEOXY-1,5-[(2,3,6-TRI-O-BENZYL-4-DEOXY-1-O-METHYL-4-α-D-GLUCOPYRANOSYL)METHYLIMINO]-D-0 GLUCITOL A solution of methyl 2,3,6-tri-O-benzyl-4-deoxy-4-trifluoromethylsulfonyloxymethyl-α-D-glucopyranoside (1 g, 1.64 mmol) and 2,3,6-tri-O-benzyl-1,5-dideoxy-1,5-imino-D-glucitol (0.71 g, 1.64 mmol) in ethanol-free chloroform (60 mL) is refluxed under nitrogen during 48 h. The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-1,5-[(2,3,6-tri-O-benzyl-4-deoxy-1-O-methyl-4-α-D-glucopyranosyl)-methylimino]-D-glucitol as a foam.

EXAMPLE XXX

Preparation of 1,5-DIDEOXY-1,5-[(4-DEOXY-1-O-METHYL-4-α-D-GLUCOPYRANOSYL)METHYLIMINO]-D-GLUCITOL The amine 2,3,6-tri-O-benzyl-1,5-dideoxy-1,5-[(2,3,6-tri-O-benzyl-4-deoxy-1-O-methyl-4-α-D-glucopyranosyl)methylimino]-D-glucitol (0.98 g, 1.09 mmol) is dissolved in methanol (20 mL). Cyclohexene (10 mL) and palladium hydroxyde 20% on charcoal (0.8 g) are added and the mixture is refluxed under nitrogen during 8 h. The catalyst is removed by filtration and the solvents are evaporated under reduced pressure. Flash chromatography on silica gel and elution with a graded mixture of chloroform, methanol and water will afford the expected amine 1,5-dideoxy-1,5-[(4-deoxy-1-O-methyl-4-α-D-glucopyranosyl)methylimino]-D-glucitol as an amorphous solid.

EXAMPLE XXXI

Preparation of 2,3,6-TRI-O-BENZYL-D-GALACTOPYRANOSE

Methyl 2,3,6-tri-O-benzyl-α-D-galactopyranoside (5 g, 10.75 mmol) is dissolved at 0° C. in a 9:1 mixture of trifluoroacetic acid and water (50 mL) (N. Morishima, S. Koto, M. Oshima, A. Sugimoto and S. Zen, Bull Chem. Soc. Jpn 56, 2849 (1983)). The mixture is stirred overnight at 0° C. The solvents are evaporated under reduced pressure without heating. The residue is dissolved in ethyl acetate and washed successively with sodium bi-carbonate and brine. The organic layer is dried over sodium sulfate, filtered and concentrated under reduced pressure so as to afford an oil. Flash chromatography on silica gel and elution with a graded mixture of ethyl acetate and hexane will afford 2,3,6-tri-O-benzyl-D-galactopyranose as an oil.

EXAMPLE XXXII

Preparation of
1,4-DI-O-ACETYL-2,3,6-TRI-O-BENZYL-D-GALACTOPYRANOSE 2,3,6-tri-O-benzyl-D-galactopyranose(3.927 g, 8.72 mmol) is dissolved in dry pyridine (25 mL) and acetic anhydride (5 mL) is added. The mixture is stirred during 24 h at room temperature. The solvent is evaporated under high vacuum. The residue is dissolved in ethyl acetate and washed with water. The organic layer is dried over sodium sulfate, filtered and concentrated under reduced pressure so as to afford the expected diacetate 1,4-di-O-acetyl-2,3,6-tri-O-benzyl-D-galactopyranose (4.64 g, 99%) as an oil which can be used without purification.

EXAMPLE XXXIII

Preparation of
4-O-ACETYL-2,3,6-TRI-O-BENZYL-α-D-GALACTOPYRANOSYL CHLORIDE

A solution of 1,4-di-O-acetyl-2,3,6-tri-O-benzyl-D-galactopyranose (4.64 g, 8.67 mmol) in ether (10 mL) is treated with ethereal hydrogen chloride (0.2 g/mL, 25 mL). The mixture is stirred at room temperature during 48 h. The solvents are evaporated under reduced pressure so as to afford an oil. Flash chromatography on silica gel and elution with a graded mixture of carbon tetrachloride and ethyl acetate will afford 4-O-acetyl-2,3,6-tri-O-benzyl-α-D-galactopyranosyl chloride as an oil.

EXAMPLE XXXIV

Preparation of METHYL
4-O-(4-O-ACETYL-2,3,6-TRI-O-BENZYL-α-D-GALACTOPYRANOSYL)-2,3,6-TRI-O-BENZYL-α-D-GLUCOPYRANOSIDE Ethereal silver perchlorate (0.08 M, 84.5 mL, 6.76 mmol) is added with stirring at −30° C. to a solution of methyl-2,3,6-tri-O-benzyl-α-D-glucopyranoside (2.284 g, 4.93 mmol) (P. J. Garegg, H. Hultberg and S. Wallin, Carbohydr. Res., 108, 97 (1982)), 4-O-acetyl-2,3,6-tri-O-benzyl-α-D-galactopyranosyl chloride (3.142 g, 6.154 mmol) and 2,4,6-trimethylpyridine (0.89 mL, 6.76 mmol) in ether (20 mL). The mixture is stirred 15 min at −30° C. and silver chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 4-O-(4-O-acetyl-2,3,6-tri-O-benzyl-α-D-galactopyranosyl)-2,3,6-tri-O-benzyl-α-D-glucopyranoside as a foam.

EXAMPLE XXXV

Preparation of METHYL
2,3,6-TRI-O-BENZYL-4-O-(2,3,6-TRI-O-BENZYL-α-D-GALACTOPYRANOSYL)-α-D-GLUCOPYRANOSIDE Methyl 4-O-(4-O-acetyl-2,3,6-tri-O-benzyl-α-D-galacto-pyranosyl)-2,3,6-tri-O-benzyl-α-D-glucopyranoside (2.543 g, 2.71 mmol) is dissolved in hot toluene (20 mL) and methanol (80 mL) is added, followed by a few drops of 1 M methanolic sodium methoxide. The mixture is stirred at room temperature during 2 h. The reaction mixture is made neutral with Amberlite IR 120 (H+) resin, filtered and concentrated under reduced pressure so as to afford methyl 2,3,6-tri-O-benzyl-4-O-(2,3,6-tri-O-benzyl-α-D-galactopyranosyl)-α-D-glucopyranoside as an amorphous solid.

EXAMPLE XXXVI cl Preparation of METHYL 4-O-(2,3,6-TRI-O-BENZYL-4-O-TRIFLUOROMETHYLSULFONYL-α-D-GALACTOPYRANOSYL)-2,3,6-TRI-O-BENZYL-α-D-GLUCOPYRANOSIDE To a solution of dry pyridine (0.49 mL) in dry methylene chloride (40 mL) cooled to −15° C. is added trifluoromethanesulfonic anhydride (0.91 mL). The mixture is stirred during 15 min at −10° C., then methyl 2,3,6-tri-O-benzyl-4-O-(2,3,6-tri-O-benzyl-α-D-galactopyranosyl)-α-D-glucopyranoside (2.428 g, 2.71 mmol) in methylene chloride (10 mL) is added. The mixture is stirred during 1.5 h at −10° C. The reaction mixture is washed with water. The organic layer is dried over sodium sulfate, filtered and concentrated under reduced pressure so as to afford an oil which will be the expected triflate methyl 4-O-(2,3,6-tri-O-benzyl-4-O-tri-fluoromethylsulfonyl-α-D-galactopyranosyl)-2,3,6-tri-O-benzyl-α-D-glucopyranoside.

EXAMPLE XXXVII

Preparation of
2,3,6-TRI-O-BENZYL-1,5-DIDEOXY-N-[2,3,6-TRI-O-BENZYL-4-DEOXY-1-(2,3,6-TRI-O-BENZYL-1-O-METHYL-4-O-α-D-GLUCOPYRANOSYL)-α-D-GLUCOPYRANOSYL]-1-5-IMINO-D-GLUCITOL A solution of methyl 4-O-(2,3,6-tri-O-benzyl-4-O-trifluoromethysulfonyl-α-D-galactopyranosyl)-2,3,6-tri-O-benzyl-α-D-glucopyranoside (1.52 g, 1.46 mmol) and 2,3,6-tri-O-benzyl-1,5-dideoxy-1,5-imino-D-glucitol (0.632 g, 1.46 mmol) in ethanol-free chloroform (50 mL) is refluxed under nitrogen during 48 h. The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-[2,3,6-tri-O-benzyl-4-deoxy-1-(2,3,6-tri-O-benzyl-1-O-methyl-4-O-α-D-glucopyranosyl)-α-D-glucopyranosyl]-1,5-imino-D-glucitol as an amorphous solid.

EXAMPLE XXXVIII

Preparation of
1,5-DIDEOXY-N-[4-DEOXY-1-(1-O-α-METHYL-4-O-α-D-GLUCOPYRANOSYL)-α-D-GLUCOPYRANOSYL]-1,5-IMINO-D-GLUCITOL 2,3,6-tri-O-benzyl-1,5-dideoxy-N-[2,3,6-tri-O-benzyl-4-deoxy-1-(2,3,6-tri-O-benzyl-1-O-methyl-4-O-α-D-glucopyranosyl)-α-D-glucopyranosyl]-1,5-imino-D-glucitol (1 g, 0.762 mmol) is dissolved in methanol (30 ml). Palladium hydroxyde 20% on charcoal (0.5 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-[4-deoxy-1-(1-O-methy-4-O-α-D-glucopyranosyl)-α-D-glucopyranosyl]-1,5-imino-D-glucitol as an amorphous solid.

EXAMPLE XXXIX

Preparation of
1-ETHENYL-1,2:3,4-DI-O-ISOPROPYLIDENE-β-D-ARABINOPYRANOSE

To a solution of oxalyl chloride (1.05 mL, 17.22 mmol) in dry tetrahydrofuran (40 mL) cooled to −78° C., dry dimethyl sulfoxyde (1.3 mL, 18.04 mmol) is added dropwise and then stirred during 35 min at −35° C. The reaction mixture is cooled again to −78° C. and 2,3:4,5-di-O-isopropylidene-D-fructopyranose (4.26 g, 16.4 mmol) (R. F. Brady, Carbohydr. Res., 15, 35 (1970)) dissolved in tetrahydro-furan (20 mL) is added and the mixture is stirred during 15 min at −35° C., then triethylamine (11.5 mL, 82.65 mmol) is added and the mixture is stirred during 1 h at −35° C. This aldehyde can be used without purification and isolation in a Wittig reaction described as follows. To dried triphenylmethylphosphonium bromide (11.7 g, 32.8 mmol) suspended in tetrahydrofuran (400 mL) is added dropwise at −78° C. a 1.55 M solution of n-butyllithium in hexane (21 mL, 32.66 mmol). The reaction mixture is warmed to room temperature and stirred during 1.5 h. Then the mixture is cooled to 0° C. and potassium tertio-butylate (3.68 g, 32.8 mmol) and dry tertio-butyl alcohol (3 mL, 31.8 mmol) are added. The mixture is stirred again at room temperature during 30 min. The reaction mixture is cooled to −78° C. and the tetrahydrofuran solution of the aldehyde prepared above is added dropwise. The reaction mixture is warmed to room temperature and stirred during 2 h. A saturated aqueous solution of ammonium chloride and the solvents are evaporated under reduced pressure. The residue is dissolved in ether and washed with water. The organic layer is dried over sodium sulfate, filtered and concentrated under reduced pressure so as to afford a brown oil. Flash chromatography on silica gel and elution with a graded mixture of hexane and ethyl acetate will afford the expected olefine 1-ethenyl-1,2:3,4-di-O-isopropylidene-β-D-arabinopyranose as an oil.

EXAMPLE XL

Preparation of
1,2:3,4-DI-O-ISOPROPYLIDENE-1-(2-HYDROXYETHYL)-β-D-ARABINOPYRANOSE To a solution of 1-ethenyl-1,2:3,4-di-O-isopropylidene-β-D-arabinopyranose (2 g, 7.81 mmol) in dry tetrahydrofuran (15 mL) is added a 10 M solution of borane in methyl sulfide (0.78 mL, 7.8 mmol) at 0° C. under nitrogen. The mixture is stirred during 3 h at room temperature. The excess of borane is destroyed with ethanol (3 mL). The mixture is cooled at 0° C. 30% hydrogen peroxyde (1 mL) and 3 N aqueous solution of sodium hydroxyde (1 mL) are added. The mixture is refluxed during 2 h. The reaction mixture is diluted with water and extracted three times with ethyl acetate. The organic layer is dried over sodium sulfate, filtered and concentrated under reduced pressure so as to afford an oil. Flash chromatography on silica gel and elution with a 1:1 mixture of ethyl acetate and hexane will afford the expected alcohol 1,2:3,4-di-O-isopropylidene-1-(2-hydroxyethyl)-β-D-arabinopyranose as an oil.

EXAMPLE XLI

Preparation of
1,2:3,4-DI-O-ISOPROPYLIDENE-1-(2-IODOETHYL)-α-D-ARABINO PYRANOSE

To a solution of 1,2,3,4-di-O-isopropylidene-1-(2-hydroxyethyl)-α-D-arabinose (1.7 g, 6.2 mmol) in dry methylene chloride (30 mL) is added triethylamine (1.3 mL, 9.3 mmol). Then the mixture is cooled to −10° C. and mesylchloride (0.5 mL, 6.46 mmol) is added dropwise. The mixture is stirred an additional 15 min at −10° C., then the reaction is allowed to warm up to room temperature. The mixture is washed three times with water. The organic phase is dried over sodium sulfate, filtered and concentrated under reduced pressure so as to afford a yellow oil which can be used without purification. The crude 1,2,3,4-di-O-isopropylidene-1-(2-methylsulfonyloxyethyl)-α-D-arabinose is dissolved in ether (15 mL). To this mixture a 0.35 M solution of magnesium iodide in ether (53 mL) is added at 0° C. The mexture is stirred 15 min at 0° C. The excess of magnesium iodide is hydrolyzed with water. The reaction mixture is washed with aqueous sodium thiosulfate and water. The organic layer is dried over sodium sulfate, filtered and concentrated under reduced pressure so as to afford an oil. Flash chromatography on silica gel and elution with a 911 mixture of hexane and ethylacetate will afford the expected iodide 1,2:3,4-di-O-isopropylidene-1-(2-iodoethyl)-β-D-arabinopyranose as a slightly yellow oil.

EXAMPLE XLII

Preparation of
2,3,6-TRI-O-BENZYL-1,5-DIDEOXY-1,5-{[2-(1,2,3,4-DI-O-ISOPROPYLIDENE-1-β-D-ARABINOPYRANOSYL)ETHYL]IMINO}-D-GLUCITOL A solution of 1,2:3,4-di-O-isopropylidene-1-(2-iodoethyl)-β-D-arabinose (1.9 g, 4.95 mmol) and 2,3,6-tri-O-benzyl-1,5-dideoxy-1,5-imino-D-glucitol (0.714 g, 1.65 mmol) in dry dimethylformamide (10 mL) is heated at 80° C. overnight along with dry potassium carbonate (0.91 g, 6.6 mmol). The dimethylformamide is evaporated under reduced pressure. The residue is taken with ethyl acetate and washed twice with water. The organic layer is dried over sodium sulfate, filtered and concentrated under reduced pressure so as to afford an oil. Chromatography on neutral aluminum oxyde activity III and elution with a graded mixture of hexane and ethyl acetate will afford the expected amine 2,3,6-tri-O-benzyl-1,5-dideoxy-1,5{[2-(1,2,3,4-di-O-isopropylidene-1-β-D-arabinopyranosyl)]imino}-D-glucitol as a foam.

EXAMPLE XLIII

Preparation of
2,3,6-TRI-O-BENZYL-1,5-DIDEOXY-1,5-{[2-(1-O-METHYL-1-α-D-ARABINOFURANOSYL)ETHYL]IMINO}-D-GLUCITOL 2,3,6-tri-O-benzyl-1,5-dideoxy-1,5-{[2-(1,2:3,4-di-O-isopropylidene-1-β-D-arabinopyranosyl)ethyl]imino}-D-glucitol (0.739 g, 1.072 mmol) is dissolved in methanol (60 mL) containing 5% of dry hydrochloric acid and is refluxed during 24 h. The reaction mixture is cooled to room temperature and neutralized with Amberlyst A26 OH⁻ form. The mixture is filtered and the solvent is evaporated under reduced pressure so as to give a foam. Flash chromatography on silica gel and elution with a graded mixture of ethylacetate and methanol will afford the expected amine 2,3,6-tri-O-benzyl-1,5-dideoxy-1,5-{[2-(1-O-methyl-1-α-D-arabinofuranosyl)ethyl]-imino}-D-glucitol as a foam.

EXAMPLE XLIV

Preparation of
1,5-DIDEOXY-1,5-{[2-(1-O-METHYL-1-α-D-ARABINOFURANOSYL)ETHYL]-IMINO}-D-GLUCITOL The amine 2,3,6-tri-O-benzyl-1,5-dideoxy-1,5-{[2-(1-O-methyl-1-α-D-arabinofuranosyl)ethyl]imino}-D-glucitol (0.4 g, 0.642 mmol) is dissolved in a 9:1 mixture of methanol and water (20 mL). Palladium hydroxyde 20% on charcoal (0.2 g) is added and the mixture is hydrogenated during 4 days at atmospheric pressure. The catalyst is removed by filtration and the solvents are evaporated under reduced pressure. Flash chromatography on silica gel and elution with a graded mixture of chloroform, methanol and water will afford the expected amine 1,5-dideoxy-1,5-([2-(1-O-methyl-1-α-D-arabinofuranosyl)ethyl]-imino}-D-glucitol as an amorphous solid.

EXAMPLE XLV

Preparation of METHYL
6-O-(4-O-ACETYL-2,3,6-TRI-O-BENZYL-α-D-GALACTOPYRANOSYL)-2,3,4-TRI-O-BENZYL-α-D-GLUCOPYRANOSIDE Ethereal silver perchlorate (0.08 M, 76.9 mL, 6.15 mmol) is added with stirring at −30° C. to a solution of methyl 2,3,4-tri-O-benzyl-α-D-glucopyranoside (2.078 g, 4.48 mmol), 4-O-acetyl-2,3,6-tri-O-benzyl-α-D-galactopyranosyl chloride (2.859 g, 5.6 mmol) and 2,4,6-trimethylpyridine (0.81 mL, 6.15 mmol) in ether (20 mL). The mixture is stirred 15 min at −30° C. and silver chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 6-O-(4-O-acetyl-2,3,6-tri-O-benzyl-α-D-galactopyranosyl)-2,3,4-tri-O-benzyl-α-D-glucopyranoside as a foam.

EXAMPLE XLVI

Preparation of METHYL
2,3,4-TRI-O-BENZYL-6-O-(2,3,6-TRI-O-BENZYL-α-D-GALACTOPYRANOSYL)-α-D-GLUCOPYRANOSIDE Methyl 6-O-(4-O-acetyl-2,3,6-tri-O-benzyl-α-D-galactopyranosyl)-2,3,4-tri-O-benzyl-α-D-glucopyranoside (2.314 g, 2.46 mmol) is dissolved in hot toluene (20 mL) and methanol (80 mL) is added, followed by a few drops of 1 M. methanolic sodium methoxide. The mixture is stirred at room temperature during 2 h. The reaction mixture is made neutral with Amberlite IR 120 (H⁺) resin, filtered and concentrated under reduced pressure so as to afford methyl 2,3,4-tri-O-benzyl-6-O-(2,3,6-tri-O-benzyl-α-D-galactopyranosyl)-α-D-glucopyranoside as an amorphous solid.

EXAMPLE XLVII

Preparation of METHYL
6-O-(2,3,6-TRI-O-BENZYL-4-O-TRIFLUOROMETHYLFULFONYL-α-D-GALACTOPYRANOSYL)-2,3,4-TRI-O-BENZYL-α-D-GLUCOPYRANOSIDE To a solution of dry pyridine (0.45 mL) in dry methylene chloride (40 mL) cooled to −15° C. is added trifluoromethanesulfonic anhydride (0.83 mL). The mixture is stirred during 15 min at −10° C., then methyl 2,3,4-tri-O-benzyl-6-O-(2,3,6- o tri-O-benzyl-α-D-galactopyranosyl)-α-D-glucopyranoside (2.21 g, 2.46 mmol) in methylene chloride (10 mL) is added. The mixture is washed with water. The organic layer is dried over sodium sulfate, filtered and concentrated under reduced pressure so as to afford an oil which will be the expected triflate methyl 6-O-(2,3,6-tri-O-benzyl-4-O-trifluoromethylsulfonyl-α-D-galactopyranosyl)-2,3,4-tri-O-benzyl-α-D-glucopyranoside.

EXAMPLE XLVIII

Preparation of
2,3,6-TRI-O-BENZYL-1,5-DIDEOXY-N-[2,3,6-TRI-O-BENZYL-DEOXY-1-(2,3,4-TRI-O-BENZYL-1-O-METHYL-6-O-α-D-GLUCOPYRANOSYL)-α-D-GLUCOPYRANOSYL]-1,5-IMINO-D-GLUCITOL A solution of methyl 6-O-(2,3,6-tri-O-benzyl-4-O-trifluoromethysulfonyl-α-D-galactopyranosyl)-2,3,4-tri-O-benzyl-α-D-glucopyranoside (1.6 g, 1.55 mmol) and 2,3,6-tri-O-benzyl-1,5-dideoxy-1,5-imino-D-glucitol (0.671 g, 1.55 mmol) in ethanol-free chloroform (50 mL) is refluxed under nitrogen during 48 h. The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-[2,3,6-tri-O-benzyl-4-deoxy-1-(2,3,4-tri-O-benzyl-1-O-methyl-6-O-α-D-glucopyranosyl)-α-D-glucopyranosyl]-1,5-imino-D-glucitol as an amorphous solid.

EXAMPLE XLIX

Preparation of
1,5-DIDEOXY-N-[4-DEOXY-1-(1-O-METHYL-6-O-
-α-D-GLUCOPYRANOSYL)-α-D-
GLUCOPYRANOSYL]-1,5-IMINO-D-GLUCITOL 2,3,6-tri-O-benzyl-1,5-dideoxy-N-[2,3,6-tri-O-benzyl 4-deoxy-1-(2,3,4-tri-O-benzyl-1-O-methyl-6-O-α-D-glucopyranosyl)-α-D-glucopyranosyl]-1,5-imino-D-glucitol (1.2 g, 0.915 mmol) is dissolved in methanol (30 mL). Palladium hydroxyde 20% on charcoal (0.6 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-[4-deoxy-1-(1-O-methyl-6-O-α-D-glucopyranosyl)-α-D-glucopyranosyl]-1,5-imino-D-glucitol as an amorphous solid.

EXAMPLE L

Preparation of
2,3,6-TRI-O-BENZYL-4-DEOXY-4-HYDROX-
YMETHYL-D-GLUCOPYRANOSE

Methyl 2,3,6-tri-O-benzyl-4-deoxy-4-hydroxymethyl-α-D-glucopyranoside (4.78 g, 10 mmol) is dissolved at 0° C. in a 9:1 mixture of trifluoracetic acid and water (50 mL). The mixture is stirred overnight at 0° C. The solvents are evaporated under reduced pressure without heating. The residue is dissolved in ethyl acetate and washed successively with sodium bicarbonate and brine. The organic layer is dried over sodium sulfate, filtered and concentrated under reduced pressure so as to afford an oil. Flash chromatography on silica gel and elution with a graded mixture of ethyl acetate and hexane will afford 2,3,6-tri-O-benzyl-4-deoxy-4-hydroxymethyl-D-glucopyranose as an oil.

EXAMPLE LI

Preparation of ACETYL
2,3,6-TRI-O-BENZYL-4-DEOXY-4-ACETYLOX-
YMETHYL-D-GLUCOPYRANOSIDE 2,3,6-tri-O-benzyl-4-deoxy-4-hydroxymethyl-D-glucopyranose (5.10 g, 9.30 mmol) is dissolved in dry pyridine (25 mL) and acetic anhydride (5 mL) is added. The mixture is stirred during 24 h at room temperature. The solvent is evaporated under high vacuum. The residue is dissolved in ethyl acetate and washed with water. The organic layer is dried over sodium sulfate, filtered and concentrated under reduced pressure so as to afford the expected diacetate acetyl 2,3,6-tri-O-benzyl-4-deoxy-4-acetyloxymethyl-D-glucopyranoside as an oil which is used without purification.

EXAMPLE LII

Preparation of
2,3,6-TRI-O-BENZYL-1,4-DIDEOXY-4-
ACETYLOXYMETHYL-D GLUCOPYRANOSYL
CHLORIDE Acetyl 2,3,6-tri-O-benzyl-4-deoxy-4-acetyloxymethyl-D-glucpyranoside (5.10 g, 9.30 mmol) in ether (10 mL) is treated with ethereal hydrogen chloride (0.2 g/mL, 25 mL). The mixture is stirred at room temperature during 48 h. The solvents are evaporated under reduced pressure so as to afford an oil. Flash chromatography on silica gel and elution with a graded mixture of carbon tetrachloride and ethyl acetate will afford 2,3,6-tri-O-benzyl-1,4-dideoxy-4-acetyloxymethyl-D-glucopyranosyl chloride as an oil.

EXAMPLE LIII

Preparation of METHYL
4-O-(2,3,6-TRI-O-BENZYL-4-DEOXY-4-
ACETYLOXYMETHYL-α-D-
GLUCOPYRANOSYL)-2,3,6-TRI-O-BENZYL-α-D-
GLUCOPYRANOSIDE Ethereal silver perchlorate (0.08 M, 9.58 mL, 7.67 mmol) is added with stirring at −30° C. to a solution of methyl 2,3,6-tri-O-benzyl-α-D-glucopyranoside (2.592 g, 5.59 mmol), 2,3,6-tri-O-benzyl 1,4-dideoxy-4-acetyloxymethyl-D-glucopyranosyl chloride (3.661 g, 6.98 mmol) in ether (20 mL). The mixture is stirred 15 min at −30° C. and silver chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 4-O-(2,3,6-tri-O-benzyl-4-deoxy-4-acetyloxymethyl-α-D-glucopyranosyl)-2,3,6-tri-O-benzyl-α-D-glucopyranoside as a foam.

EXAMPLE LIV

Preparation of METHYL
4-O-(2,3,6-TRI-O-BENZYL-4-DEOXY-4-HYDROX-
YMETHYL-α-D-GLUCOPYRANOSYL)-2,3,6-TRI-
O-BENZYL-α-D-GLUCOPYRANOSIDE Methyl 4-O-(2,3,6-tri-O-benzyl-4-deoxy-4-acetyloxymethy-α-D-glucopyranosyl)-2,3,6-tri-O-benzyl-α-D-glucopyranoside (3.19 g, 3.35 mmol) is dissolved in hot toluene (20 mL) and methanol (80 mL) is added, followed by a few drops of 1 M. methanolic sodium methoxide. The mixture is stirred at room temperature during 2 h. The reaction mixture is made neutral with Amberlite IR 120 (H+) resin, filtered and concentrated under reduced pressure so as to afford methyl 4-O-(2,3,6-tri-O-benzyl-4-deoxy-4-hydroxymethyl-α-D-glucopyranosyl)-2,3,6-tri-O-benzyl-α-D-glucopyranoside as an amorphous solid.

EXAMPLE LV

Preparation of METHYL
4-O-(2,3,6-TRI-O-BENZYL-4-DEOXY-4-TRI-
FLUOROMETHYLSULFONYLOXMETHYL-α-D-
GLUCOPYRANOSYL)-2,3,6-TRI-O-BENZYL-α-D-
GLUCOPYRANOSIDE To a solution of dry pyridine (0.6 mL) in dry methylene chloride (50 mL) cooled to -15° C. is added trifluoromethanesulfonic anhydride (1.12 mL). The mixture is stirred during 15 min at −10° C., then methyl 4-O-(2,3,6-tri-O-benzyl-4-deoxy-4-hydroxymethyl-α-D-glucopyranosyl)-2,3,6-tri-O-benzyl-α-D-glucopyranoside (3.049g, 3.35 mmol) in methylene chloride (15 mL) is added. The mixture is washed with water. The organic layer is dried over sodium sulfate, filtered and concentrated under reduced pressure so as to afford an oil which will be the expected triflate methyl 4-O-(2,3,6-tri-O-benzyl-4-deoxy-4-trifluoromethylsulfonyloxymethyl-α-D-glucopyranosyl)-2,3,6-tri-O-benzyl-α-D-glucopyranoside.

EXAMPLE LVI

Preparation of
2,3,6-TRI-O-BENZYL-1,5-DIDEOXY-N-{[2,3,6-TRI-O-BENZYL-4-DEOXY-1-(2,3,6-TRI-O-METHYL-4-O-α-D-GLUCOPYRANOSYL)-4-α-D-GLUCOPYRANOSYL]METHYL}1,5-IMINO-D-GLUCITOL A solution of methyl 4-O-(2,3,6-tri-O-benzyl-4-deoxy-4-trifluoromethylsulfonyloxymethyl-α-D-glucopyranosyl)-2,3,6-tri-O-benzyl-α-D-glucopyranoside (1.82 g, 1.75 mmol) and 2,3,6-tri-O-benzyl-1,5-dideoxy-1,5-imino-D-glucitol(0.758 g, 1.75 mmol) in ethanol-free chloroform (50 mL) is refluxed under nitrogen during 48 h. The mixture is diluted in methylene chloride and washed successively with a saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-{[2,3,6-tri-O-benzyl-4-deoxy-1-(2,3,6-tri-O-benzyl-4-O-α-D-glucopyranosyl)-4-α-D-glucopyranosyl]methyl}-1,5-imino-D-glucitol as an amorphous solid.

EXAMPLE LVII

Preparation of
1,5-DIDEOXY-N-{[4-DEOXY-1-(1-O-METHYL-4-O-α-D-GLUCOPYRANOSYL)-4-α-D-GLUCOPYRANOSYL]METHYL}1,5-IMINO-D-GLUCITOL 2,3,6-tri-O-benzyl-1,5-dideoxy-N-{[2,3,6-tri-O-benzyl-4-deoxy-1-(2,3,6-tri-O-benzyl-1-O-methyl-4-O-α-D-glucopyranosyl)-4-α-D-glucopyranosyl]methyl}1,5-imino-D-glucitol (1.3 g, 1.247 mmol) is dissolved in methanol (40 mL). Palladium hydroxyde 20% on charcoal (0.6 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-([4-deoxy-1-(1-O-methyl-4-O-α-D-glucopyranosyl)-4-α-D-glucopyranosyl]methyl}1,5-imino-D-glucitol as an amorphous solid.

EXAMPLE LVIII

Preparation of METHYL
6-O-(2,3,6-TRI-O-BENZYL-4-DEOXY-4-ACETYLOXYMETHYL-α-D-GLUCOPYRANOSYL)-2,3,4-TRI-O-BENZYL-α-D-GLUCOPYRANOSIDE Ethereal silver perchlorate (0.08 M, 76.7 mL, 6.13 mmol) is added with stirring at −30° C. to a solution of methyl 2,3,4-tri-O-benzyl-α-D-glucopyranoside (2.074 g, 4.472 mmol), 2,3,6-tri-O-benzyl-1,4-dideoxy-4-acetyloxymethyl-D-gluco-pyranosyl chloride (6.13 mmol) and 2,4,6-trimethylpyridine (0.80 mL, 6.13 mmol) in ether (20 mL). The mixture is stirred 15 min at −30° C. and silver chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 6-O-(2,3,6-tri-O-benzyl-4-deoxy-4-acetyloxymethyl-α-D-glucopyranosyl)-2,3,4-tri-O-benzyl-α-D-glucopyranoside as a foam.

EXAMPLE LIX

Preparation of (1 METHYL
6-O-(2,3,6-TRI-O-BENZYL-4-DEOXY-4-HYDROXYMETHYL-α-GLUCOPYRANOSYL)-2,3,4-TRI-O-BENZYL-α-D-GLUCOPYRANOSIDE Methyl 6-O-(2,3,6-tri-O-benzyl-4-deoxy-4-acetyloxymethyl-α-D-glucopyranosyl)-2,3,4-tri-O-benzyl-α-D-glucopyranoside (2.469 g, 2.593 mmol) is dissolved in hot toluene (20 mL) and methanol (80 mL) is added, followed by a few drops of 1 M methanolic sodium methoxide. The mixture is stirred at room temperature during 2 h. The reaction mixture is made neutral with Amberlite IR 120 (H+) resin, filtered and concentrated under reduced pressure so as to afford methyl 6-O-(2,3,6-tri-O-benzyl-4-deoxy-4-hydroxymethyl-α-D-glucopyranosyl)-2,3,4-tri-O-benzyl-α-D-glucopyranoside as an amorphous solid.

EXAMPLE LX

Preparation of METHYL
6-O-(2,3,6-TRI-O-BENZYL-4-DEOXY-4-TRIFLUOROMETHYLSULFONYLOXYMETHYL-α-D-GLUCOPYRANOSYL)-2,3,4-TRI-O-BENZYL-α-D-GLUCOPYRANOSIDE To a solution of dry pyridine (0.46 mL) in dry methylene chloride (40 mL) cooled to −15° C. is added trifluoromethanesulfonic anhydride (0.86 mL). The mixture is stirred during 15 min at −10° C., then methyl 6-O-(2,3,6-tri-O-benzyl-4-deoxy-4-hydroxymethyl-α-D-glucopyranosyl)2,3,4-tri-O-benzyl-α-D-glucopyranoside (2.36 g, 2.593 mmol) in methylene chloride (10 mL) is added. The mixture is stirred during 1.5 h at −10° C. The reaction mixture is washed with water. The organic layer is dried over sodium sulfate, filtered and concentrated under reduced pressure so as to afford an oil which will be the expected triflate methyl 6-O-(2,3,6-tri-O-benzyl-4-deoxy-4-trifluoromethylsulfonyloxymethyl-α-D-glucopyranosyl)-2,3,4-tri-O-benzyl-α-D-glucopyranoside.

EXAMPLE LXI

Preparation of
2,3,6-TRI-O-BENZYL-1,5-DIDEOXY-N-{[2,3,6-TRI-O-BENZYL-4-DEOXY-1-(2,3,4-TRI-O-BENZYL-1-O-METHYL-6-O-α-D-GLUCOPYRANOSYL)-4-α-D-GLUCOPYRANOSYL]METHYL}1,5-IMINO-D-GLUCITOL A solution of methyl 6-O-(2,3,6-tri-O-benzyl-4-deoxy-4-trifluoromethylsulfonyloxymethyl-α-D-glucopyranosyl)-2,3,4-tri-O-benzyl-α-D-glucopyranoside (1.8 g, 1.72 mmol) and 2,3,6-tri-O-benzyl-1, 5-dideoxy-1,5-imino-D-glucitol (0.745 g, 1.72 mmol) in ethanol-free chloroform (50 mL) is refluxed under nitrogen during 48 h. The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-{[2,3,6-tri-O-benzyl-4-deoxy-1-(2,3,4-tri-O-benzyl-1-O-methyl-6-O-α-D-glucopyranosyl)-4-α-D-glucopyranosyl]methyl}1,5-imino-D-glucitol as an amorphous solid.

EXAMPLE LXII

Preparation of
1,5-DIDEOXY-N-{[4-DEOXY-1-(1-O-METHYL-6-O-α-D-GLUCOPYRANOSYL)-4-α-D-GLUCOPYRANOSYL]METHYL}1,5-IMINO-D-GLUCITOL 2,3,6-tri-O-benzyl-1,5-dideoxy-N-{[2,3,6-tri-O-benzyl-4-deoxy-1-(2,3,4-tri-O-benzyl-1-O-methyl-6-O-α-D-glucopyranosol)-4-α-D-glucopyranosyl]methyl}1,5-imino-D-glucitol (1.3 g, 1.247 mmol}is dissolved in methanol (30 mL). Palladium hydroxyde 20% on charcoal (0.6 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-{[4-deoxy-1-(1-O-methyl-6-O-α-D-glucopyranosyl)-4-α-D-glucopyranosyl]methyl}1,5-imino-D-glucitol as an amorphous solid.

EXAMPLE LXIII

Preparation of
1,5-DIDEOXY-1,5-(6-DEOXY-6-D-GLUCOPYRANOSYL}IMINO-D-GLUCITOL 1,5-dideoxy-1,5-(6-deoxy-1-O-methyl-6-α-D-glucopyranosyl) imino-D-glucitol (0.150 g, 0.442 mmol) is dissolved in a 1:1 mixture of water and trifluoroacetic acid (10 mL). The mixture is stirred during 24 h at 0° C. The solvents are evaporated under reduced pressure so as to afford a foam. Chromatography on Amberlyst A26 OH⁻ form will afford the expected amine 1,5-dideoxy-1,5-(6-deoxy-6-D-glucopyranosyl)imino-D-glucitol.

EXAMPLE LXIV

Preparation of
5-AZIDO-3,6-DI-O-BENZYL-5-DEOXY-D-GLUCOFURANOSE

The azide 5-azido-3,6-di-O-benzyl-5-deoxy-1,2-O-isopropylidene-α-D-glucofuranoside (U. G. Nayak and R. L. Whisler, J. Org. Chem., 33, 3582 (1968) (15.02 g, 35.3 mmol) was dissolved at 0° C. in 100mL of a 9:1 mixture of trifluoroacetic acid and water. The mixture was stirred at 0° C. during 2 h. The trifluoroacetic acid was evaporated under reduced pressure at room temperature. The residue was taken with ether and washed with water. The organic layer was dried over sodium sulfate, filtered and concentrated under reduced pressure. Flash chromatography on silica gel and elution with a 1:1 mixture of hexane and ethyl acetate, followed by re-crystallization in a mixture of hexane and ethyl acetate afforded the expected compound 5-azido-3,6-di-O-benzyl-5-deoxy-D-glucofuranose.

EXAMPLE LXV

Preparation of METHYL
5-AZIDO-3,6-DI-O-BENZYL-5-DEOXY-D-GLUCOFURANOSIDE

To a solution of 5-azido-3,6-di-O-benzyl-5-D-glucofuranose (10.23 g, 26.5 mmol) in methylene chloride (170 mL) was added methanol (11 mL) and borontrifluoroetherate (1.5 mL). The mixture was stirred 24 h at room temperature. The reaction mixture was successively washed with a saturated aqueous solution of sodium bicarbonate and then with brine. The organic layer was dried over sodium sulfate, filtered and concentrated under reduced pressure. Flash chromatography on silica gel and elution with a 1:1 mixture of hexane and ethyl acetate afforded methyl 5-azido-3,6-di-O-benzyl-5-deoxy-D-glucofuranoside as a colorless oil (9.15 g, 85%).

EXAMPLE LXVI

Preparation of METHYL
5-AZIDO-2,3,6-TRI-O-BENZYL-5-DEOXY-D-GLUCOFURANOSIDE

To a suspension of sodium hydride (1.2 g, 27.5 mmol), 55% in mineral oil, washed three times with pentane) in anhydrous tetrahydrofuran (200 mL) was added quickly dropwise the alcohol methyl 5-azido-3,6-di-O-benzyl-5-deoxy-D-gluco-furanoside (9.15 g, 22.9 mmol) in tetrahydrofuran (50 mL) at room temperature and under nitrogen. The mixture was stirred during 3 h at room temperature. The mixture was yellow. Then n-Bu₄N⁺I⁻ (76 mg, 0.20 mmol) was added followed by benzyl bromide (3.30 mL, 27.5 mmol) added dropwise. The mixture was stirred overnight at room temperature. After hydrolysis with saturated aqueous ammonium chloride tetrahydrofuran was evaporated under reduced pressure. The residue was diluted with water and extracted three times with ether. The organic phase was dried over sodium sulfate. Filtration and evapo-ration under reduced pressure afforded an oil. Flash chromatography on silica gel and elution with a 20:80 mixture of ethyl acetate and hexane afforded the expected compound methyl 5-azido-2,3,6-tri-O-benzyl-5-deoxy-D-glucofuranoside as a colorless oil (10.88 g, 97%).

EXAMPLE LXVII

Preparation of
5-AZIDO-2,3,6-TRI-O-BENZYL-5-DEOXY-D-GLUCOFURANOSE

Methyl 5-azido-2,3,6-tri-O-benzyl-5-deoxy-D-glucofuranoside (10.8 g, 22.2 mmol) was dissolved at room temperature in tetrahydrofuran (20 mL). The solution was cooled at −10° C. and trifluoroacetic acid (120 mL) was added dropwise followed by addition of water (20 mL). The mixture was stirred at 0° C. during 24 h. The mixture was evaporated under reduced pressure without heating. The residue was taken with ether and washed with water. The organic layer was dried over sodium sulfate, filtered and concentrated under reduced pressure. Flash chromatography on silica gel and elution with a 20:80 mixture of ethyl acetate and hexane afforded 5-azido-2,3,6-tri-O-benzyl-5-deoxy-D-glucofuranose as a colorless oil (9.63 g, 90%).

EXAMPLE LXVIII

Preparation of
5-AZIDO-2,3,6-TRI-O-BENZYL-5-DEOXY-D-GLUCONIC ACID-γ-LACTONE

To a solution of the lactol 5-azido-2,3,6-tri-O-benzyl-5-deoxy-D-glucofuranose (9.36 g, 20 mmol) in acetone (240 mL) cooled to 0° C., Jones' reagent 2 M (11.5 mL) was added dropwise until the color was orange. The excess of Jones' reagent was destroyed with 2-propanol (0.5 mL). The mixture was concentrated under reduced pressure. The residue was taken with water and extracted with ether. The organic phase was dried with sodium sulfate, filtered and concentrated under reduced pressure so as to afford an oil. Flash chromatography on silica gel and elution with a 1:9 mixture of ethyl acetate and hexane afforded the γ-laclone 5-azido-2,3,6-tri-O-benzyl-5-deoxy-D-gluconic acid-γ-lactone.

EXAMPLE LXIX

Preparation of
2,3,6-TRI-O-BENZYL-5-DEOXY-D-GLUCONIC ACID-6-LACTAM

To a solution of the lactone 5-azido-2,3,6-tri-O-benzyl-5-deoxy-D-gluconic acid-γ-lactone (8.16 g, 17 mmol) in ethanol (180 mL) was added lindlar catalyst (1.7 g). The mixture was hydrogenated under atmospheric pressure during 24 h. Filtration and evaporation under reduced pressure afforded an oil which was crystallized in a mixture of hexane and ether. The lactam 2,3,6-tri-O-benzyl-5-deoxy-D-gluconic acid-δ-lactam was obtained as white crystals (7.4 g, 96%). mp: 85°–85.5° C.

In a similar manner, by following the teachings of the foregoing examples, there will be produced the following specific compounds.

1,5-Dideoxy-1,5-[6,7-dideoxy-7-D-glucoheptopyranosyl)imino]-D-glucitol;
1,5-Dideoxy-1,5-[(1-deoxy-D-fructofuranosyl)imino]-D-glucitol;
1,5-Dideoxy-1,5-[(4-deoxy-4-D-glucopyranosyl)imino]-D-glucitol;
1,5-Dideoxy-N-[6-deoxy-1-(6-O-D-glucopyranosyl)-α-D-glucopyranosyl]-1,5-imino-D-glucitol;
1,5-Dideoxy-N-[6,7-dideoxy-1-(6-O-D-glucopyranosyl)-7-α-D-glucoheptopyranosyl]-1,5-imino-D-glucitol;
1,5-Dideoxy-1,5-[(4-deoxy-4-D-glucopyranosyl)methylimino]-D-glucitol;
1,5-Dideoxy-N-[4-deoxy-1-(4-O-D-glucopyranosyl)-α-D-glucopyranosyl]-1,5-imino-D-glucitol;
1,5-Dideoxy-1,5-{[2(1-D-arabinofuranose)ethyl]imino}-D-glucitol;
1,5-Dideoxy-N-[4-deoxy-1-(6-O-D-glucopyranosyl)-α-D-glucopyranosyl]-1,5-imino-D-glucitol;
1,5-Dideoxy-N-{[4-deoxy-1-(4-O-D-glucopyranosyl)-4-α-D-glucopyranosyl]methyl}-1,5-imino-D-glucitol;
1,5 Dideoxy-N-{[4-deoxy-1-(6-O-D-91ucopyranosyl)-4-α-D-glucopyranosyl]methyl}-1,5-imino-D-glucitol;
1,5-Dideoxy-1,5-[(6-deoxy-1-O-methyl-6-β-D-glucopyranosyl)-imino-D-glucitol;
1,5-Dideoxy-1,5-[(6,7-dideoxy-1-O-methyl-7-β-D-glucoheptopyranosyl)imino]-D-glucitol;
1,5-Dideoxy-1,5-[(1-deoxy-2-O-methyl-β-D-fructofuranosyl)-imino]-D-glucitol;
1,5-Dideoxy-1,5-[(4-deoxy-1-O-methyl-4-β-D-glucopyranosyl)imino]-D-glucitol;
1,5-Dideoxy-N-[6-deoxy-1-(1-O-methyl-6-O-β-D-glucopyranosyl)-α-D-glucopyranosyl]-1,5-imino-D-glucitol;
1,5-Dideoxy-N-[6,7-dideoxy-1-(1-O-methyl-6-O-β-D-glucopyranosyl)-7-α-D-glucoheptopyranosyl]-1,5-imino-D-glucitol;
1,5-Dideoxy-1,5-[(4-deoxy-1-O-methyl-4-β-D-glucopyranosyl)-methylimino]-D-glucitol;
1,5-Dideoxy-N-[4-deoxy-1-(1-O-methyl-4-O-β-D-glucopyranosyl)-α-D-glucopyranosyl]-1,5-imino-D-glucitol;
1,5-Dideoxy-1,5-{[2-O-methyl-1-β-D-arabinofuranosyl)ethyl]-imino}-D-glucitol;
1,5-Dideoxy-N-[4-deoxy-1-(1-O-methyl-6-O-β-D-glucopyranosyl)-α-D-glucopyranosyl]-1,5-imino-D-glucitol;
1,5-Dideoxy-N-{[4-deoxy-1-(1-O-methyl-4-O-β-D-glucopyranosyl)-4-α-D-glucopyranosyl]methyl}-1,5-imino-D-glucitol;
1,5-Dideoxy-N-{[4-deoxy-1-(1-O-methyl-6-O-β-D-glucopyranosyl)-4-α-D-glucopyranosyl]methyl}-1,5-imino-D-glucitol;
1,5-Dideoxy-1,5-[(7-deoxy-1-O-methyl-7-L-glycero-α-D-glucoheptopyranosyl)imino]-D-glucitol;
1,5-Dideoxy-1,5-[(7-deoxy-1-O-methyl-7-α-glycero-α-D-glucoheptopyranosyl)imino]-D-glucitol.

Enzymes which catalyze the hydrolysis of complex carbohydrates, e.g. α-glycosidases, convert non-absorbable carbohydrates into absorbable sugars. The rapid action of these enzymes, particularly following the intake of high levels of carbohydrates, lead to acute high levels in blood glucose which, in the case diabetics, lead to undesirable manifestations, thus it has been a long-sought goal to find compounds which will obviate the hyperglicemia caused by dietary improprieties. Similarly, in the case of obesity the control of high levels of blood glucose, with its subsequent conversion to fat, caused by the catalysis of carbohydrates has inspired the quest for compounds which will obviate the problems associated with dietary improprieties.

The compounds of this invention (I) are potent and longlasting inhibitors of α-glucosidase and, by standard laboratory methods for determining serum glucose levels, are shown to be useful for the treatment of disease states caused by the underutilization and/or overproduction of serum glucose without adversely affecting the rate of transport across cell membranes. Thus, the compounds are useful in the treatment of diabetes and obesity.

In the practice of this invention, an effective amount of a compound of this invention is that amount required to reduce the amount of serum glucose (relative to a control) following the ingestion of carbohydrates convertible to absorbable glucose. The specific dosage for the treatment of any specific patient suffering from either disease state will depend upon such factors as size, type and age of the patient as well as the severity of the disease state, all of which are factors normally familiar to and considered by the attending diagnostician treating the patient. Generally, the compounds are to be administered orally at a dose of 0.2 to 20 milligrams per kilogram of body weight (MPK) with a dose of 0.5 to 5 MPK being preferred. The compounds preferable are to be administered orally at mealtimes in single or multiple unit doses containing 25 mg to 250 mg. Of course, in the treatment of obesity, the term includes the practice of the disease as well as continuel administration of dose regimens suitable for the maintenance of the desired weight for the patient.

It is also to be found that the compounds of the instant invention (I) will exert an inhibitory effect on glycosidase enzymes that are essential for elaboration of the final structure of the oligosaccharide side chains of glyco proteins, particularly the HIV (gp 120) glycoprotein. Suitable assay techniques, e.g. syncytial formation, the reverse transcriptase assay, immunofluorescence tests and election microscopy, may be used to evaluate the effects on HIV viral growth and for determining dose regimens. Antiviral effects may be confirmed by immunofluorescence with serum for virally infected patients. In the treatment of the HIV related disease states, as well as other retroviral glyco protein-related disease states, unlike the treatment of diabetes and obesity, the compounds of this invention may be administered by parenteral means; specific doses being within the above stated dose range for treatment of diabetes and obesity.

In practising the end use application of the compounds of this invention, the compounds are preferably incorporated in a pharmaceutical formulation comprising a pharmaceutical carrier in admixture with a compound of this invention. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups emulsions, dispersions and wettable and effervescent powders, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa.

What is claimed is:

1. 1-deoxy nojirimycin derivatives of the formula

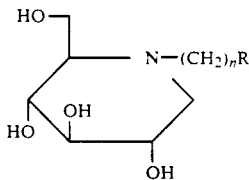

and the pharmaceutically acceptable acid addition salts thereof wherein n is zero, 1 or 2 and R is a glycosyl moiety, which is a radical having from 1 to 3 hexose, pentose or heptose units which, if desired, may further comprise an ether or an acyl radical at the anomeric carbon atom of the terminal hexose or pentose moiety.

2. A compound of claim 1 wherein R is a glucosyl, galactosyl, fucosyl, fructosyl, mannosyl, ribosyl, arabinosyl, xylosyl, allosyl, altrosyl, gulosyl, idosyl, talosyl, lyxosyl, isomaltosyl, trehalosyl, β cellobiosyl, maltosyl, maltotriosyl or cellotriosyl radical.

3. A compound of claim 1 wherein R is 6-glucosyl, 4-glucosyl, 1-fructosyl, 6-fructosyl, 6-maltosyl, 4-maltosyl, 6-isomaltosyl or 4-isomaltosyl.

4. A compound of claim 1, said compound being 1,5-dideoxy-1,5-[(6-deoxy-1-O-methyl-6-α-D-glucopyranosyl)-imino]-D-glucitol.

5. A compound of claim 1, said compound being 1,5-dideoxy-1,5-[(6,7-dideoxy-1-O-methyl-7-α-D-glucoheptopyranosyl)imino]-D-glucitol.

6. A compound of claim 1, said compound being 1,5-di-deoxy-1,5-[(1-deoxy-2-O-methyl-α-D-fructofuranosyl)imino]-D-glucitol.

7. A compound of claim 1, said compound being 1,5-dideoxy-1,5-[(4-deoxy-1-O-methyl-4-α-D-glucopyranosyl)-imino]-D-glucitol.

8. A compound of claim 1, said compound being 1,5-dideoxy-N-[6-deoxy-1-(1-O-methyl-6-O-α-D-glucopyranosyl)-α-D-glucopyranosyl]-1,5-imino-D-glucitol.

9. A compound of claim 1, said compound being 1,5-dideoxy-N-[6,7-dideoxy-1(1-O-methyl-6-O-α-D-glucopyranosyl)-7-α-D-glucoheptopyranosyl]-1,5-imino-D-glucitol.

10. A compound of claim 1, said compound being 1,5-di-deoxy-1,5-[(4-deoxy-1-O-methyl-4-α-D-glucopyranosyl)methyl-imino]-D-glucitol.

11. A compound of claim 1, said compound being 1,5 di-deoxy-N-[4-deoxy-1-(1-O-methyl-4-O-α-D-glucopyranosyl)-α-D-glucopyranosyl 1.5-imino-D-glucitol.

12. A compound of claim 1, said compound being 1,5-di-deoxy-1,5-{[2-(1-O-methyl-1-α-D-arabinofuranosyl)ethyl]imino}-D-glucitol.

13. A compound of claim 1, said compound being 1,5-di-deoxy-N-[4-deoxy-1-(1-O-methyl-6-O-α-D-glucopyranosyl)-α-D-glucopyranosyl]-1,5-imino-D-glucitol.

14. A compound of claim 1, said compound being 1,5-di-deoxy-N-[4-deoxy-1-(1-O-methyl-4-O-α-D-glucopyranosyl)-4-α-D-glucopyranosyl]methyl}-1,5-imino-D-glucitol.

15. A compound of claim 1, said compound being 1,5-di-deoxy-N-{[4-deoxy-1-(1-O-methyl-6-O-α-D-glucopyranosyl)-4-α-D-glucopyranosyl]methyl}-1,5-imino-D-glucitol.

16. A compound of claim 1, said compound being 1,5-di-deoxy-1,5-(6-deoxy-6-D-glucopyranosyl)imino-D-glucitol.

17. A compound of claim 1, said compound being 1,5-di-deoxy-1,5-[(7-deoxy-1-O-methyl-7-L-glycero-α-D-gluco-heptopyranosyl)imino]-D-glucitol.

18. A compound of claim 1, said compound being 1,5-di-deoxy-1,5-[(7-deoxy-1-O-methyl-7-L-glycero-α-D-gluco-heptopyranosyl)imino]-D-glucitol.

19. A method for inhibiting o-glucosidase enzymes which comprises administering thereto an effective amount of a compound of claim 1.

20. A method for treating diabetes which comprises administering to a patient suffering from a diabetes a therapeutically effective amount of a compound of claim 1.

21. A method for controlling obesity which comprises administering to a patient an amount of a compound of claim 1 sufficient to reduce the amount of systematically absorbable glucose following ingestion of food substances capable of being enzymatically converted to glucose.

22. A pharmaceutical composition suitable for use in the treatment of diabetes or obesity which comprises a compound of claim 1 in admixture with a pharmaceutical carrier.

23. A process for the preparation of a compound of the formula

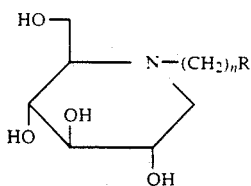

and the pharmaceutically acceptable acid addition salts thereof, wherein n is zero, one or two, and R is a glycosyl or etherified or acylated glycosyl radical containing from 1 to 3 hexose or pentose units, said glycosyl radical which, if desired, may further comprise an ether or ester derivative of the hydroxyl moiety located on the anomeric carbon atom of the terminal hexose or pentose moiety, which comprises reacting a compound of the formula

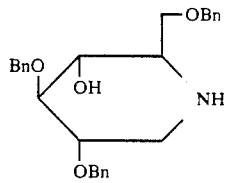

with a compound of the formula

R'(CH$_2$)$_n$X      III wherein X is a halide or triflate and n is zero, one or two and R' is a hydroxy-protected glycosyl moiety which, i'desired, may further comprise an acyl or ether radical at the anomeric carbon atom of the terminal hexose or pentose moiety to form a compound of the formula

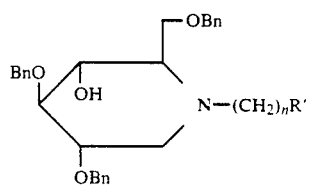

which is deprotected by standard deprotection techniques.

24. The compound of claim 1 wherein R is a glycosyl moiety, which is a radical having from 1 to 3 hexose or pentose units.

* * * * *

UNITED STATES PATENT AND TRADEMARK OFFICE
CERTIFICATE OF CORRECTION

PATENT NO. : 5,157,116

DATED : October 20, 1992

INVENTOR(S) : Jean-Bernard Ducep and Charles Danzin

It is certified that error appears in the above-identified patent and that said Letters Patent is hereby corrected as shown below:

At column 1, line 42, the patent reads "salts forms" and should read "salt forms". At column 1, line 67, the patent reads "comtemplated" and should read "contemplated". At column 2, line 18, the patent reads "$C_{-8}$" and should read "$C_{1-8}$". At column 8, lines 24-25, the patent reads "6,7 dideoxy-" and should read "6,7-dideoxy-". At column 10, line 30, the patent reads "dexoy-2-Omethyl-" and should read " deoxy-2-O-methyl-". At column 11, line 20, the patent reads "amine 0,3,6-" and should read "amine 2,3,6-". At column 11, line 65, reads "methyl2,3,4-" and should read --methyl-2,3,4-"-- column 12, line 40, "11 TM" should be deleted. At column 15, line 22, the patent reads "Glycopyranoside" and should read "Glucopyranoside". At column 15, line 51, the patent reads "upwith" and should read "up with". At column 16, lines 16-17, the patent reads "-D-0-Glucitol" and should read "D-Glucitol". At column 18, line 20, the patent reads "Example XXXVI cl" and should read "Example XXXVI". At column 19, line 18, the patent reads "O-methy-4" and should read "O-methyl-4". At column 20, line 36, the patent reads "mexture" and should read "mixture". At column 20, line 42, the patent reads "a 911 mixture" and should read "a 9:1 mixture". At column 22, line 32, the patent reads "(2,3,6-o tri-O" and should read "(2,3,6-tri-O". At column 23, line 60, the patent reads "-D Glucopyranosyl" and should read "-D-Glucopyranosyl". At column 23, line 63, the patent reads "glupyranoside" and should read "glucopyranoside". At column 24, line 15, the patent reads "-benzyl 1,4" and should read "-benzyl-1,4". At column 24, line 38, the patent reads "acetyloxymethy-α" and should read "acetyloxymethyl-α".

UNITED STATES PATENT AND TRADEMARK OFFICE
CERTIFICATE OF CORRECTION

PATENT NO. : 5,157,116

DATED : October 20, 1992

INVENTOR(S) : Jean-Bernard Ducep and Charles Danzin

It is certified that error appears in the above-identified patent and that said Letters Patent is hereby corrected as shown below:

At column 25, line 15, the patent reads "glucitol(0.758" and should read "glucotol (0.758". At column 26, line 11, the patent reads "(1 Methyl" and should read "Methyl". At column 28, line 42, the patent reads "evapo-ration" and should read "evaporation". At column 29, line 59, "9lucopyranosyl) should read --glucopyranosyl)--. At column 30, line 12, the patent reads "{[2-O-methyl" and should read {[2-(1-O-methyl". At column 32, line 48, claim 18, the patent reads "-7-L-glycero" and should read "-7-D-glycero". At column 34, line 16, claim 23, the patent reads "i'desired" and should read "if desired".

Signed and Sealed this

Twenty-fourth Day of May, 1994

BRUCE LEHMAN

Attest:

Attesting Officer

Commissioner of Patents and Trademarks